US006846486B1

(12) United States Patent
Skurkovich et al.

(10) Patent No.: US 6,846,486 B1
(45) Date of Patent: Jan. 25, 2005

(54) METHOD OF TREATING ALLERGY BY ADMINISTERING AN ANTI-HISTAMINE ANTIBODY

(75) Inventors: Boris Skurkovich, Pawtucket, RI (US); Simon V. Skurkovich, Rockville, MD (US)

(73) Assignee: Advanced Biotherapy Concepts, Inc., Rockville, MD (US)

( * ) Notice: Subject to any disclaimer, the term of this patent is extended or adjusted under 35 U.S.C. 154(b) by 0 days.

(21) Appl. No.: 09/511,972

(22) Filed: Feb. 24, 2000

(51) Int. Cl.$^7$ .............................................. A61K 39/395
(52) U.S. Cl. .................... 424/130.1; 424/85.4; 424/85.5
(58) Field of Search .............................. 424/85.4, 85.5, 424/130.1, 134.1; 514/826, 885

(56) References Cited

U.S. PATENT DOCUMENTS

| 4,902,506 A | 2/1990 | Anderson et al. |
| 5,023,243 A | 6/1991 | Tullis |
| 5,034,506 A | 7/1991 | Summerton et al. |
| 5,168,053 A | 12/1992 | Altman et al. |
| 5,190,931 A | 3/1993 | Inouye |
| 5,840,869 A | 11/1998 | Mosley et al. |
| 5,858,682 A | 1/1999 | Gruenwald et al. |

FOREIGN PATENT DOCUMENTS

| WO | WO92/07065 | 4/1992 |
| WO | WO94/17810 | 8/1994 |
| WO | WO94/23744 | 10/1994 |
| WO | 95/26365 | 10/1995 |

OTHER PUBLICATIONS

Stratagene Catalog, 1988, p. 39.*
Horsmanheimo et al. J. Allergy Clin Immunol. 1996, 98: 408–411.*
deVries JE, "Novel Fundamental Approaches To Intervening In IgE–Mediated Allergic Diseases," J. Invest. Dermatol. pp. 141–144, 1994, 102(2).
Pierkes et al., "Decreased release of histamine and sulfidoleukotrienes by human peripheral blood leukocytes after wasp venom immunotheraphy is partially due to induction of IL–10 and IFN–γ production of T cells," J.Allergy Clin. Immunology 151(1) pp 52–64 (1993).
Ikizawa et al., "Inhibition of IL–4 receptor up–regulation on B cells by antisense oligodeoxynucleotide suppresses IL–4–induced human IgE production," Clin. Exp. Immunology 1995, 100(3) pp. 383–389.
Renz et al., "Inhibition Of Allergen–Induced IgE and IgG1 Production By Soluble IL–4 Receptor," Int.Arch.Allergy Immunol. 106(1) pp 46–54 (1995).
Haruna et al., "The Secondary Antigen–Specific IgE Response in Murine Lymphocytes Is Resistant To Blockade by Anti–IL4 Antibody and an Antisense Oligodeoxynucleotide for IL4 mRNA," Cellular Immunology 151(1) pp. 52–64 (1993).

Chan et al., "Altered Prostaglandin $E_2$ Regulation Of Cytokine Production In Atopic Dermatitis," J.Immunol. 151 pp 3345–3352 (1993).
Raz et al., "Preferential Induction of a $Th_1$ immune response and inhibition of specific IgE antibody formation by plasmid DNA immunization," Proc. Natl.Acad.Sci. vol. 93, pp. 5141–5145 (1996).
Barbas, 1995, Nature Medicine 1:837–839.
Bini et al., 1999, Mayo Clin. Proc. 74:367–370.
Burger et al., 1991, J. Gen. Virol. 72:359–367.
Burton et al., 1994, Adv. Immunol. 57:191–280.
Carelli et al., 1992, Biomed. and Pharmacother. 46:149–153.
Cech et al., 1992, J. Biol. Chem. 267:17479–17482.
Cech, 1988, J. Amer. Med. Assn. 260:3030.
Chu et al., 1983, Infn. Immun. 40:245–256.
Coffman, 1996, In: Cytokine Regulation of Humoral Immunity, pp. 379–389, Snapper, ed., John Wiley and Sons, New York.
Coffman and Carty, 1986, J. Immunol. 136:949–954.
Cohen, 1993, Science 259:1691–1692.
Cranage et al., 1986, EMBO J. 5:3057–3063.
de Kruif et al. 1995, J. Mol. Biol. 248:97–105.
Drazen et al., 1999, New Eng. J. Med. 340:197–206.
Finkelman et al., 1986, Proc. Natl. Acad. Sci. USA 83:9675–9678.
Finkelman et al., 1988, J. Immunol. 140:1022–1027.
Finkelman et al., 1988, J. Immunol. 141:2335–2341.
Fynan et al., 1993, Proc. Natl. Acad. Sci. 90:11478–11482.
Hagiwara and Klinman (1996, In: Cytokine Regulation of Humoral Immunity, pp. 409–430, Snapper, ed., John Wiley and Sons, New York.
Hampel and Tritz, 1989, Biochemistry 28:4929–4933.
Hasselhoff and Gerlach, 1988, Nature 334:585.
Huston et al., 1988, Proc. Natl. Acad. Sci. U.S.A. 85:5879–5883.
Kay et al., 1997, Int. Arch. Allergy Immunol. 113:196–199.
Lee et al., 1997, J. Exp. Med. 185:2143–2156.

(List continued on next page.)

Primary Examiner—Prema Mertz
(74) Attorney, Agent, or Firm—Morgan, Lewis & Bockius, LLP

(57) ABSTRACT

The present invention relates to allergy vaccines and methods of treating and/or preventing asthma, and allergic conditions. The invention is based on the discovery that inhibiting the ligand/receptor interactions involving, e.g., IgE, IL-3, IL-4, IL-5, IL-6, IL-10, IL-13, interferon-alpha, histamine, leukotriene, and their respective receptors, inhibits production of IgE thereby treating or preventing such diseases or conditions. Competitive inhibition of such receptor/ligand interactions is accomplished by immunizing a human or veterinary patient with the interleukin, interferon-alpha, histamine, leukotriene, their receptors, in any combination. Also, the invention relates to inhibiting receptor/ligand interactions involved in IgE production by competitively inhibiting such interactions by administering antibodies to the ligands, receptors, or both, as well as by administering analogs of the receptors (e.g., soluble receptors not associated with a cell).

3 Claims, No Drawings

OTHER PUBLICATIONS

King et al., 1989, Proc. Natl. Acad. Sci. USA 86:10085–10089.
Krasnowska et al., 1992, Arch. Immunol. Ther. Exp. (Warsz) 40:75–78.
Kuhn et al., 1991, Science 254:707–710.
Kung et al., 1995, Inflamm. Res. 44:S185–S186.
Marcus–Sakura, 1988, Anal. Biochem. 172:289.
Marks et al., 1991, J. Mol. Biol. 222:581–597.
Nielson et al., 1991, Science 254:1497.
Pearce et al., 1990, Thorax 45:170–175.
Reilly et al., 1997, Clin. Pharmacol. 32:313–323.
Romagnani, 1994, Annu. Rev. Immunol. 12:227–257.
Sanderson et al., 1986, Proc. Natl. Acad. Sci. USA 83:437–440.
Seder and Gurunathan, 1999, New. Eng. J. Med. 341:277–278.
Sher and Coffman, 1992, Annu. Rev. Immunol. 10:385–409.
Snapper, 1996, In: Cytokine Regulation of Humoral Immunity, pp. 324–346.
Snapper, ed., John Wiley and Sons, New York; de Vries and Punnonen, Ibid. at pp. 195–215 Tanaka et al., 1996, In: Cytokine Regulation of Humoral Immunity, pp. 251–272, Snapper, ed., John Wiley and Sons, New York.
Thompson–Snipes et al., 1991, J. Exp. Med. 173:507–510.
von der Weid et al., 1994, Eur. J. Immunol. 24:2285–2293.
Weintraub, 1990, Scientific American 262:40.
Wierenga et al., 1990, J. Immunol. 144:4651–4656.
Wolff et al., 1991, Biotechniques 11:474–485.
Wright et al., 1992, Critical Rev. Immunol. 12:125–168.
Yssel et al., 1992, J. Immunol. 148:738–745.

* cited by examiner

METHOD OF TREATING ALLERGY BY ADMINISTERING AN ANTI-HISTAMINE ANTIBODY

BACKGROUND OF THE INVENTION

The development of allergy or other types of immune hypersensitivity is an important undesirable effect of acquired immunity in mammals, particularly humans. There are several types of allergy. The present invention is concerned with atopic allergy. Atopic allergy is characterized by an excess production of IgE antibody, which attaches to mast cells and basophils. A single mast cell or basophil may bind as many as a half a million molecules of IgE. When an antigen binds to at least two IgE molecules bound on the surface of a mast cell or a basophil, the cell ruptures or otherwise is caused to release several substances including histamine, leukotrienes (previously referred to as "slow reacting substance of anaphylaxis"), eosinophilic chemotactic factor, proteases, neutrophil chemotactic substance, heparin, platelet activating factors and bradykinin. Release of these substances results in dilation of local blood vessels, attraction of eosinophils and neutrophils to the reactive site, damage to local tissues by proteases, increased permeability of the capillaries and loss of fluid into the tissues, and contraction of smooth muscle cells. A number of different abnormal tissue responses ensue including anaphylaxis, urticaria, hay fever and asthma.

In anaphylaxis, a widespread allergic reaction occurs throughout the vascular system and in closely associated tissues. Body-wide vasodilation as well as increased permeability of the capillaries with resultant marked loss of plasma from the circulation occurs. Death may result from circulatory shock within minutes. In addition, leukotrienes are released which may elicit a massive asthma attack and death by suffocation.

Urticaria results when an antigen enters specific skin areas and causes local anaphylactoid reactions and skin swelling commonly known as "hives."

In hay fever, the allergic reaction occurs in the nose. Histamine released in response to the reaction causes local vascular dilation, with resultant increased capillary pressure as well as increased capillary permeability. Both of these effects cause rapid fluid leakage into the tissues of the nose and the nasal linings become swollen and secretory.

Asthma is characterized by spastic contraction of the smooth muscle in the bronchioles, which causes extreme difficulty in breathing. Asthma occurs in 3 to 5 percent of all people at some time in their life. The usual cause of asthma is hypersensitivity of the bronchioles to foreign substances in the air. About 70 percent of the asthma which occurs in younger patients, i.e., those under 30 years of age, is caused by allergic hypersensitivity, in particular, by sensitivity to plant pollens. In older persons, the cause of asthma is almost always hypersensitivity to non-allergic type irritants such as air pollution and the like.

The three hallmark features of allergic disease are the presence of excessive mast cells and eosinophils, and the production of IgE. The cytokines responsible for this activity are interleukin 4 (IL-4A) for IgE production (Finkelman et al., 1986, Proc. Natl. Acad. Sci. USA 83:9675–9678; Coffman et al., 1986, J. Immunol. 136:949–954), IL-5 in the case of eosinophilia (Sanderson et al., 1986, Proc. Natl. Acad. Sci. USA 83:437–440), and the combination of IL-3, IL-4, and IL-10 in the case of mast cell production (Thompson-Snipes et al., 1991, J. Exp. Med. 173:507–510).

The initiation of the immune response to a pathogen requires a complex series of interactions among certain cell populations generally involving cytokine production as reviewed by Gause and Lu (1996, In: Cytokine Regulation of Humoral Immunity, Snapper, ed., John Wiley and Sons, New York). Within hours after immunization with a pathogen, a highly pronounced and restricted cytokine pattern is detectable in lymphoid organs. Generally, the immune response may be classified according to the CD4+ T-helper (Th) cells associated therewith as either a type I response, mediated by T-helper type 1 cells (Th1), or type 2 response, mediated by T-helper type 2 cells. More recently, it has been demonstrated that the type 1 and type 2 responses may each be mediated by cells other than Th1 or Th2.

The type 1 response involves Th1-type cytokines including IFN-γ and IL-2 and, since IFN-γ is a mediator for activation of macrophages and monocytes, the type 1 response is associated with cellular immunity and inflammation. In contrast, Th2 cells are mediators of Ig production (humoral immunity) and produce IL-4, IL-5, IL-6, IL-9, IL-10, and IL-13 (Tanaka et al., 1996, In: Cytokine Regulation of Humoral Immunity, pp. 251–272, Snapper, ed., John Wiley and Sons, New York). However, the cellular and humoral immunity compartments are intertwined as exemplified by the role of IL-6 in both responses which is mediated by complex interactions between various cells and the cytokines produced thereby. It has been demonstrated that interaction of Th2 cells with B cells induces a humoral response (characterized by Ig production) in that IL-4 signaling through CD40 induces IL-6 production which enhances Ig synthesis. In contrast, interaction of Th1 cells with macrophages or monocytes causes production of, inter alia, IL-6 which, in turn, causes an inflammatory response. Therefore, certain cytokines may play a role in both humoral and cellular immune responses and the production of cytokines orchestrates a highly complex series of responses.

Of the humoral responses, the immune response mediated by IgE has been the most studied perhaps due to the fact that IgE mediates a unique and potent set of effector functions that are central features of allergy and asthma. The principal cellular pathway leading to IgE production involves B-cell activation via CD40-IL-4 signaling causing B cells to class switch to IgE. In mice, there is compelling evidence that IL-4 is required for virtually all primary IgE responses. More specifically, treatment of mice with an excess of anti-IL-4 neutralizing antibody inhibits 95–99% of primary IgE response to various stimuli (Finkelman et al., 1986, Proc. Natl. Acad. Sci. U.S.A. 83:9675–9678; Finkelman et al., 1988, J. Immunol. 141:2335–2341; Finkelman et al., 1988, J. Immunol. 140:1022–1027). Additionally, IFN-γ and antibodies to IL-5 and IL-4 inhibit pulmonary eosinophilia in allergic mice sensitized by ovalbumin challenge (Kung et al., 1995, Inflamm. Res. 44:S185–S186). Further, homozygous deletion transgenic mice lacking the IL-4 gene have only trace amounts of IgE after infection with various pathogens known to stimulate IgE production (Kuhn et al., 1991, Science 254:707–710; von der Weid et al., 1994, Eur. J. Immunol. 24:2285–2293). Also, Lee et al. (1997, J. Exp. Med. 185:2143–2156) demonstrated that transgenic mice which constitutively express IL-5 develop many of the pathologies associated with asthmatic patients including eosinophil invasion of peribronchial spaces, epithelial hypertrophy, goblet cell hyperplasia, increased mucus production, and exhibit eosinophil recruitment to the airway lumen at levels comparable to asthmatic patients. Thus, these studies confirm the crucial role of IL-4 and other type 2 cytokines in IgE switching in mice and, more importantly, in the etiology of allergic disease.

Although the role of IL-4 in IgE switching and/or the development of allergic disease in humans is not as clear as it is in mice, the data suggest that IL-4 and/or IL-13 are the major inducers of IgE switching in humans; further, Th2-like type 2 responses have been demonstrated in a variety of allergic and parasitic diseases (Sher and Coffman, 1992, Annu. Rev. Immunol. 10:385–409; Yssel et al., 1992, J. Immunol. 148:738–745; Romagnani, 1994, Annu. Rev. Immunol. 12:227–257; Wierenga et al., 1990, J. Immunol. 144:4651–4656; Coffman, 1996, In: Cytokine Regulation of Humoral Immunity, pp. 379–389, Snapper, ed., John Wiley and Sons, New York). In addition, the prior art suggests that various disease conditions are associated with type 2 cytokine abnormalities as summarized by Hagiwara and Klinman (1996, In: Cytokine Regulation of Humoral Immunity, pp. 409–430, Snapper, ed., John Wiley and Sons, New York). For instance, Kay et al. (1997, Int. Arch. Allergy Immunol. 113:196–199), demonstrated that IL-4 and IL-5 production by eosinophils may amplify local allergic inflammatory responses in humans. Therefore, within the complex and interactive cytokine network which regulates the magnitude, nature and duration of immune responses against self and foreign antigens, there is mounting evidence of the role of the Th2-type cytokines, IL-3, IL-4, IL-5, IL-6, IL-9, IL-10, and IL-13, in various disease states in humans including asthma.

The allergic reaction that occurs in the allergic type of asthma is believed to occur in the following manner. The typically allergic person has a tendency to synthesize large amounts of IgE antibodies. In asthma, these antibodies are mainly attached to mast cells in the lung interstitium in close association with the bronchioles and small bronchi. When pollen is inhaled by a person hypersensitive to the pollen, (i.e., to which the person has already developed IgE antibodies), the pollen reacts with the mast cell-attached antibodies and causes the cells to release several substances including histamine, leukotrines, eosinophilic chemotactic factor, and bradykinin. The combined results of the release of these factors is the production of localized edema in the walls of the bronchioles as well as secretion of thick mucus into bronchiolar lumens, and spasm of the bronchiolar smooth muscle causing the airway resistance to increase markedly.

The majority of treatments for allergies in humans involves the administration of compounds which are directed to neutralizing the effects of the substances released from mast cells or basophils. Thus, a plethora of antihistamines and other compounds are available which neutralize the effects of histamines and the like following their release from mast cells or basophils. The drawbacks of such treatments is the necessity that they are used essentially subsequent to the allergic event and do not prevent future allergic events in the patient.

Current treatment for asthma includes the administration of compounds that control the airway inflammatory component of the disease, e.g., primarily corticosteroids, sodium cromolyn, methylxanthines and leukotriene pathway modifiers (see, e.g., Drazen et al., 1999, New Eng. J. Med. 340:197–206). In addition, there are available rapid relief compositions that counteract bronchospasm, e.g., primarily beta-adrenergic agents. These compounds have several disadvantages in that there is a risk that they will not be effective and despite their administration, the asthma attack will continue. In addition, several side effects are associated with prolonged use of these type of compounds, particularly in the case of corticosteroids and beta-adrenergic agents; further, there is a progressive loss of sensitivity to these treatments after prolonged use. In severe asthma, these compounds are only of limited efficacy. Further, these compounds are non-selective, i.e., they do not specifically target the lung, therefore, side-effects affecting other organs are a potential risk. In addition, there is an increasing body of evidence which indicates there may be an increased risk of dying from bronchial asthma following prolonged treatment of asthma using long-acting beta-adrenergic agents such as fenoterol (Pearce et al., 1990, Thorax 45:170–175; Spitzer et al., 1992, New Engl. J. Med. 326:560–561).

Approximately fifteen million individuals in the U.S. suffer from asthma, and the disease is the cause of more than five thousand deaths annually in the U.S. In children, asthma represents the most prevalent chronic disease, requiring the most frequent use of emergency room visits and hospitalizations. The overall annual cost for asthma care in the U.S. is estimated to be about nine billion dollars. Asthma is the most common cause of school and work absenteeism in the U.S.

To date, there are no long-term preventative treatments available for allergies in humans. Given the fact that allergic responses, and particularly asthma, are on the rise in the human population, there is a long felt need for the development of therapies which are designed to prevent as well as treat an allergic response in a human patient. The present invention satisfies this need.

BRIEF SUMMARY OF THE INVENTION

The invention includes an allergy vaccine comprising at least one protein selected from the group consisting of an IgE, an IgE receptor, an interleukin involved in production of IgE in a mammal, a receptor for an interleukin involved in production of IgE in a mammal, an interferon-alpha, an interferon-alpha receptor, a histamine, a histamine receptor, a leukotriene, a leukotriene receptor, in a pharmaceutically-acceptable carrier.

In one aspect, the mammal is selected from the group consisting of a human, a non-human primate, a horse, a cow, a pig, a goat, a dog, a cat, a rodent.

In a further aspect, the mammal is a human.

In another aspect, the interleukin is selected from the group consisting of IL-3, IL-4, IL-5, IL-6, IL-10, and IL-13.

In yet another aspect, the interleukin is selected from the group consisting of IL-3, IL-4, IL-5, IL-6, and IL-13.

In another aspect, the interleukin is selected from the group consisting of IL-3, IL-4, IL-5, and IL-13.

In yet another aspect, the interleukin is selected from the group consisting of IL-4, IL-5, and IL-13.

In a further aspect, the interleukin is selected from the group consisting of IL-4 and IL-5.

In yet a further aspect, the interleukin is IL-4.

In another aspect, the vaccine further comprises interferon gamma.

In a further aspect, the interleukin receptor is selected from the group consisting of an IL-3 receptor, an IL-4 receptor, an IL-5 receptor, an IL-6 receptor, an IL-10 receptor, and an IL-13 receptor.

The invention also includes an allergy vaccine comprising at least one ingredient selected from the group consisting of an interleukin involved in production of IgE in a mammal, and a receptor for an interleukin involved in production of IgE in a mammal, in a pharmaceutically-acceptable carrier.

In one aspect, the vaccine further comprising interferon gamma.

The invention further includes an allergy vaccine comprising at least one ingredient selected from the group consisting of an IgE, an IgE receptor, an interferon-alpha, an interferon-alpha receptor, a histamine, a histamine receptor, a leukotriene, and a leukotriene receptor, in a pharmaceutically-acceptable carrier.

In one aspect, the vaccine further comprising interferon gamma.

The invention includes an allergy vaccine comprising at least one isolated nucleic acid encoding a protein selected from the group consisting of an IgE, an IgE receptor, an interleukin involved in production of IgE in a mammal, a receptor for an interleukin involved in production of IgE in a mammal, an interferon-alpha, an interferon-alpha receptor, a histamine, a histamine receptor, a leukotriene, a leukotriene receptor, in a pharmaceutically-acceptable carrier.

In one aspect, the vaccine further comprises interferon gamma.

In another aspect, the isolated nucleic acid further comprises a promoter/regulatory sequence operably linked thereto.

In yet another aspect, the isolated nucleic acid further comprises a vector.

The invention further includes a method of preventing an allergic response in a mammal. The method comprises administering to the mammal an allergy vaccine comprising at least one ingredient selected from the group consisting of an IgE, an IgE receptor, an interleukin involved in the production of IgE in a mammal, a receptor for an interleukin involved in the production of IgE in a mammal, an interferon alpha, an interferon alpha receptor, an interferon-alpha, an interferon-alpha receptor, a histamine, a histamine receptor, a leukotriene, and a leukotriene receptor, thereby preventing an allergic response in a mammal.

In one aspect, the interleukin is selected from the group consisting of IL-3, IL-4, IL-5, IL-6, IL-10, and IL-13.

In another aspect, the interleukin is selected from the group consisting of IL-3, IL-4, IL-5, IL-6, and IL-13.

In yet another aspect, the interleukin is selected from the group consisting of IL-3, IL-4, IL-5, and IL-13.

In another aspect, the interleukin is selected from the group consisting of IL-4, IL-5, and IL-13.

In a further aspect, the interleukin is selected from the group consisting of IL-4 and IL-5.

In yet another aspect, the interleukin is IL-4.

In another aspect, the method further comprises administering interferon gamma to the mammal.

The invention includes a method of preventing an allergic response in a mammal. The method comprises administering to the mammal an allergy vaccine comprising at least one nucleic acid encoding an ingredient selected from the group consisting of an IgE, an IgE receptor, an interleukin involved in the production of IgE in a mammal, a receptor for an interleukin involved in the production of IgE in a mammal, an interferon-alpha, an interferon-alpha receptor, a histamine, a histamine receptor, a leukotriene, and a leukotriene receptor, thereby preventing an allergic response in a mammal.

In one aspect, the isolated nucleic acid further comprises a promoter/regulatory sequence operably linked thereto.

In another aspect, the isolated nucleic acid further comprises a vector.

In yet another aspect, the method further comprises administering interferon gamma to the mammal.

The invention also includes a method of treating an allergy in a mammal. The method comprises administering to the mammal an allergy vaccine comprising at least one ingredient selected from the group consisting of an interleukin involved in the production of IgE in a mammal, and a receptor for an interleukin involved in the production of IgE in a mammal, thereby treating an allergy in a mammal.

In one aspect, the interleukin is selected from the group consisting of IL-3, IL-4, IL-5, IL-6, IL-10, and IL-13.

In another aspect, the method further comprises administering interferon gamma to the mammal.

The invention further includes a method of treating an allergy in a mammal. The method comprises administering to the mammal an allergy vaccine comprising at least one ingredient selected from the group consisting of IgE, an IgE receptor, an interferon-alpha, an interferon-alpha receptor, a histamine, a histamine receptor, a leukotriene, and a leukotriene receptor, thereby treating an allergy in a mammal.

In one aspect, the method further comprises administering interferon gamma to the mammal.

The invention includes a method of preventing an allergic response in a mammal. The method comprises administering to the mammal at least one ingredient selected from the group consisting of an anti-interleukin compound which is not an anti-interleukin antibody, wherein the interleukin is at least one interleukin involved in the production of IgE in a mammal, thereby preventing an allergic response in a mammal.

In one aspect, the anti-interleukin compound is selected from the group consisting of a soluble interleukin receptor, and an antibody to an interleukin receptor.

In another aspect, the interleukin involved in the production of IgE is selected from the group consisting of IL-3, IL-4, IL-5, IL-6, IL-10, and IL-13.

In yet another aspect, the method further comprises administering interferon gamma to the mammal.

The invention includes a method of treating an allergy in a mammal. The method comprises administering to the mammal at least one ingredient selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, thereby treating an allergy in a mammal.

In one aspect, the interleukin involved in the production of IgE is selected from the group consisting of IL-3, IL-4, IL-5, IL-6, IL-10 and IL-13.

In a further aspect, the interleukin receptor is selected from the group consisting of an IL-3 receptor, an IL-4 receptor, an IL-5 receptor, an IL-6 receptor, and IL-10 receptor, and an IL-13 receptor.

In another aspect, the antibody to an interleukin receptor is selected from the group consisting of an antibody to an IL-3 receptor, an antibody to an IL-4 receptor, an antibody to an IL-5 receptor, an antibody to an IL-6 receptor, an antibody to an IL-10 receptor, and an antibody to an IL-13 receptor.

In yet another aspect, the method further comprises administering interferon gamma to the mammal.

The invention includes a method of treating an allergy in a mammal. The method comprises administering to the mammal at least one antisense nucleic acid complementary to a nucleic acid encoding a protein selected from the group consisting of IgE, an IgE receptor, an interleukin involved in the production of IgE in a mammal, a receptor to an interleukin involved in the production of IgE in a mammal, an interferon-alpha, an interferon-alpha receptor, a histamine, a histamine receptor, a leukotriene, and a leukotriene receptor, thereby treating an allergy in a mammal.

In one aspect, the interleukin is selected from the group consisting of IL-3, IL-4, IL-5, IL-6, IL-10 and IL-13.

In another aspect, the method further comprises administering interferon gamma to the mammal.

The invention includes a kit for preventing an allergic response in a mammal. The kit comprises at least one allergy vaccine wherein the allergy vaccine comprises a protein selected from the group consisting of IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor, an applicator, and an instructional material for the use thereof.

In one aspect, the kit further comprises interferon gamma.

The invention also includes a kit for preventing an allergic response in a mammal. The kit comprises an allergy vaccine wherein the allergy vaccine comprises at least one nucleic acid encoding IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor, wherein the interleukin is at least one interleukin involved in the production of IgE, an applicator, and an instructional material for the use thereof.

In one aspect, the kit further comprises interferon gamma.

The invention includes a kit for treating an allergy in a mammal. The kit comprises an at least one ingredient selected from an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, an applicator, and an instructional material for the use thereof.

In one aspect, the kit further comprises interferon gamma.

The invention includes a kit for treating an allergy in a mammal. The kit comprises an antisense nucleic acid complementary to a nucleic acid encoding at least one ingredient selected from the group consisting of IgE, an IgE receptor, an interleukin involved in the production of IgE in a mammal, a receptor to an interleukin involved in the production of IgE in a mammal, an interferon-alpha, an interferon-alpha receptor, a histamine, a histamine receptor, a leukotriene, and a leukotriene receptor, an applicator, and an instructional material for the use thereof.

In one aspect, the kit further comprises interferon gamma.

The invention further includes a method of inhibiting production of IgE in a mammal. The method comprises administering to the mammal at least one ingredient selected from the group consisting of an IgE, an IgE receptor, an interleukin involved in the production of IgE in a mammal, a receptor for an interleukin involved in the production of IgE in a mammal, an interferon-alpha, an interferon-alpha receptor, a histamine, a histamine receptor, a leukotriene, and a leukotriene receptor, thereby inhibiting IgE production in a mammal.

In one aspect, the interleukin is selected from the group consisting of IL-3, IL-4, IL-5, IL-6, IL-10, and IL-13.

In another aspect, the method further comprises administering interferon gamma to the mammal.

The invention includes a method of inhibiting production of IgE in a mammal. The method comprises administering to the mammal at least one nucleic acid encoding a protein selected from the group consisting of an IgE, an IgE receptor, an interleukin involved in the production of IgE in a mammal, a receptor for an interleukin involved in the production of IgE in a mammal, an interferon-alpha, an interferon-alpha receptor, a histamine, a histamine receptor, a leukotriene, and a leukotriene receptor, thereby inhibiting IgE production in a mammal.

In one aspect, the method further comprises administering interferon gamma to the mammal.

The invention also includes a method of inhibiting production of IgE in a mammal. The method comprises administering to a mammal at least one ingredient selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, thereby inhibiting production of IgE in a mammal.

In one aspect, the interleukin is selected from the group consisting of IL-3, IL-4, IL-5, IL-6, IL-10 and IL-13.

In another aspect, the method further comprises administering interferon gamma to the mammal.

The invention further includes a method of inhibiting production of IgE in a mammal. The method comprises administering to the mammal at least one antisense nucleic acid complementary to a nucleic acid encoding a protein selected from the group consisting of IgE, an IgE receptor, an interleukin involved in the production of IgE in a mammal, a receptor to an interleukin involved in the production of IgE in a mammal, an interferon-alpha, an interferon-alpha receptor, a histamine, a histamine receptor, a leukotriene, and a leukotriene receptor, thereby inhibiting production of IgE in a mammal.

In one aspect, the interleukin is selected from the group consisting of IL-3, IL-4, IL-5, IL-6, IL-10 and IL-13.

In another aspect, the method further comprises administering interferon gamma to the mammal.

The invention includes a kit for inhibiting production of IgE in a mammal. The kit comprises at least one protein selected from the group consisting of IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor, an applicator, and an instructional material for the use thereof.

In one aspect, the kit further comprises interferon gamma.

The invention also includes a kit for inhibiting production of IgE in a mammal. The kit comprises an isolated nucleic acid encoding at least one protein selected from the group consisting of IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor, wherein the interleukin is at least one interleukin involved in the production of IgE, an applicator, and an instructional material for the use thereof.

In one aspect, the kit further comprises interferon gamma.

The invention further includes a kit for inhibiting production of IgE in a mammal. The kit comprises at least one ingredient selected from an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, an applicator, and an instructional material for the use thereof.

In one aspect, the kit further comprises interferon gamma.

The invention includes a kit for inhibiting production of IgE in a mammal. The kit comprises an antisense nucleic acid complementary to a nucleic acid encoding at least one ingredient selected from the group consisting of IgE, an IgE receptor, an interleukin involved in the production of IgE in a mammal, a receptor to an interleukin involved in the production of IgE in a mammal, an interferon-alpha, an interferon-alpha receptor, a histamine, a histamine receptor, a leukotriene, and a leukotriene receptor, an applicator, and an instructional material for the use thereof.

In one aspect, the kit further comprises interferon gamma.

The invention also includes a kit for preventing an allergic response in a mammal. The kit comprises a pharmaceutical composition comprising at least one allergy vaccine in an amount effective for preventing an allergic response in a mammal in a pharmaceutically acceptable carrier, wherein the allergy vaccine comprises a protein selected from the group consisting of IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor, an applicator, and an instructional material for the use thereof.

In one aspect, the kit further comprises interferon gamma.

The invention includes a kit for preventing an allergic response in a mammal. The kit comprises a pharmaceutical composition comprising an allergy vaccine in a pharmaceutically acceptable carrier in an amount effective for preventing an allergic response in a mammal, wherein the allergy vaccine comprises at least one nucleic acid encoding IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor, wherein the interleukin is at least one interleukin involved in the production of IgE, an applicator, and an instructional material for the use thereof.

In one aspect, the kit further comprises interferon gamma.

The invention further includes a kit for treating an allergy in a mammal. The kit comprising a pharmaceutical composition comprising at least one protein in an amount effective for treating an allergy in a mammal in a pharmaceutically acceptable carrier, wherein the protein is selected from an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, an applicator, and an instructional material for the use thereof.

In one aspect, the kit further comprises interferon gamma.

The invention also includes a kit for treating an allergy in a mammal. The kit comprises a pharmaceutical composition comprising an antisense nucleic acid in an amount effective for treating an allergy in a mammal in a pharmaceutically acceptable carrier, wherein the antisense nucleic acid is complementary to a nucleic acid encoding at least one ingredient selected from the group consisting of IgE, an IgE receptor, an interleukin involved in the production of IgE in a mammal, a receptor to an interleukin involved in the production of IgE in a mammal, an interferon-alpha, an interferon-alpha receptor, a histamine, a histamine receptor, a leukotriene, and a leukotriene receptor, an applicator, and an instructional material for the use thereof.

In one aspect, the kit further comprising interferon gamma. The invention includes a pharmaceutical composition comprising at least one protein selected from the group consisting of an IgE, an IgE receptor, an interleukin involved in production of IgE in a mammal, a receptor for an interleukin involved in production of IgE in a mammal, an interferon-alpha, an interferon-alpha receptor, a histamine, a histamine receptor, a leukotriene, a leukotriene receptor, in a pharmaceutically-acceptable carrier in an amount effective for preventing an allergic response in a mammal.

In one aspect, the composition further comprises interferon gamma.

The invention includes a pharmaceutical composition comprising at least one isolated nucleic acid encoding a protein selected from the group consisting of an IgE, an IgE receptor, an interleukin involved in production of IgE in a mammal, a receptor for an interleukin involved in production of IgE in a mammal, an interferon-alpha, an interferon-alpha receptor, a histamine, a histamine receptor, a leukotriene, a leukotriene receptor, in a pharmaceutically-acceptable carrier, in an amount effective for preventing an allergic response in a mammal.

In one aspect, the composition further comprises interferon gamma.

The invention includes a pharmaceutical composition comprising at least one protein in an amount effective for treating an allergy in a mammal, wherein the protein is selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, in a pharmaceutically acceptable carrier.

In one aspect, the composition further comprises interferon gamma.

The invention further includes a method of treating an allergy in a mammal. The method comprises administering to the mammal at least one first ingredient selected from the group consisting of an anti-IL-3 antibody, an anti-IL-4 antibody, an anti-IL-5 antibody, an anti-IL-6 antibody, an anti-IL-10 antibody, and an anti-IL-13 antibody, and at least one second ingredient selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal, thereby treating an allergy in a mammal.

In one aspect, the interleukin involved in the production of IgE is selected from the group consisting of IL-3, IL-4, IL-5, IL-6, IL-10 and IL-13.

In another aspect, the interleukin receptor is selected from the group consisting of an IL-3 receptor, an IL-4 receptor, an IL-5 receptor, an IL-6 receptor, and IL-10 receptor, and an IL-13 receptor.

In yet another aspect, the antibody to an interleukin receptor is selected from the group consisting of an antibody to an IL-3 receptor, an antibody to an IL-4 receptor, an antibody to an IL-5 receptor, an antibody to an IL-6 receptor, an antibody to an IL-10 receptor, and an antibody to an IL-13 receptor.

In a further aspect, the method further comprises administering interferon gamma to the mammal.

The invention includes a method of treating bronchial asthma in a human. The method comprises administering to the human at least one ingredient selected from the group consisting of an anti-interferon-alpha antibody, an anti-interferon-alpha receptor antibody, and a soluble interferon-alpha receptor, thereby treating bronchial asthma in a human.

In one aspect, the method further comprising administering to the human at least one ingredient selected from the group consisting of an anti-IgE antibody, an anti-IgE receptor antibody, and a soluble IgE receptor.

In one aspect, the method further comprises administering to the human at least one ingredient selected from the group consisting of an anti-histamine antibody, and anti-histamine receptor antibody, and a soluble histamine receptor.

In one aspect, the method further comprises administering interferon gamma to the human.

In another aspect, the method further comprises administering to the human an anti-interleukin antibody wherein the interleukin is selected from the group consisting of IL-3, IL-4, IL-5, IL-6, IL-10 and IL-13.

DETAILED DESCRIPTION OF THE INVENTION

The present invention is based on the discovery that it is possible to prevent the production of IgE in a mammal by administering a compound that will inhibit ligand/receptor interactions necessary for the production of IgE. The inhibition of IgE production, in turn, alleviates, prevents, and/or treats an allergic response in a mammal.

One skilled in the art would appreciate, based upon the disclosure provided herein, that there are various ways to inhibit production of an interleukin involved in the production of IgE. The present invention encompasses these methods.

In one aspect, the present invention discloses methods for inducing the immune system of a mammal to actively inhibit the ligand/receptor interactions associated with production of IgE, i.e., an active immunization method. In another aspect, the present invention provides a method comprising administering a substance to a mammal such that the ligand/receptor interactions that mediate production of IgE are inhibited, i.e., a passive immunization method. Both of these approaches, which can be applied individually or in concert, are more fully discussed below.

Active Allergy Vaccine Compositions
Protein-based

The invention includes eliciting an immune response to various substances (i.e., IgE, interleukins, histamines, leukotrienes, and their receptors) thereby inhibiting ligand/receptor interactions necessary for IgE production.

One skilled in the art would also appreciate that a naturally occurring compound found in the body (e.g., IgE, interleukins, histamines, leukotrienes, and their receptors) may not trigger an immune response and/or may generate an immune response which is not sufficient to inhibit the desired target ligand/receptor interactions. Therefore, as more fully discussed below, the present invention encompasses methods of rendering a naturally occurring compound immunogenic using, for example, methods well known in the art.

In one aspect, the invention includes an allergy vaccine comprising an immunogenic IgE useful for inducing an immune response (e.g., humoral, cellular, or both), which response inhibits IgE ligand/receptor interactions necessary for development of asthma, or allergic or autoimmune conditions. One skilled in the art would appreciate, based upon the disclosure provided herein, that inducing an immune response to IgE blocks the necessary IgE/IgE receptor interactions that mediate an allergic condition, disease, or reaction.

The invention further includes an allergy vaccine comprising an immunogenic IgE receptor useful for eliciting an immune response to the receptor. Similarly to generating an immune response to IgE itself, induction of an immune response to an IgE receptor blocks the IgE/IgE receptor interactions required for the production of IgE and therefore, such an immune response is useful for treating and/or preventing an allergy mediated by the effects of IgE.

Also encompassed in the invention is an allergy vaccine comprising one or more interleukins which are necessary components in the IgE production pathway in a mammal (e.g., IL-3, IL-4, IL-5, IL-6, IL-10, IL-13). Such an allergy vaccine, by inducing an immune response against one or more of these interleukins, which immune response renders the interleukin non-functional, diminishes production of IgE in the mammal. The invention therefore includes generating an immune response by administering at least one immunogenic interleukin.

Therefore, one skilled in the art would appreciate, based upon the disclosure provided herein, that an allergy vaccine encompasses the following combinations of interleukins involved in the IgE production pathway. That is, preferably, IL-4 can be administered in concert with IL-5. Similarly, IL-4, IL-5 and IL-13 can be administered in concert. Likewise, IL-4, IL-5, IL-13 and IL-3 can be administered in concert. Further, IL-4, IL-5, IL-13, IL-3 and IL-6 can be administered in concert. Moreover, IL-4, IL-5, IL-13, IL-6 and IL-10 can be administered in concert. The invention also encompasses IL-3, IL-4, IL-5, IL-6, IL-10 and IL-13 being administered in concert. The skilled artisan would understand, based upon the disclosure provided herein, that the invention is not limited to these particular combination but encompasses an allergy vaccine comprising any combination of these interleukins. Further, the invention encompasses an allergy vaccine comprising these interleukins individually (e.g., IL-3 alone, IL-4 alone, IL-5 alone, IL-6 alone, IL-10 alone, and IL-13 alone).

Further, the invention encompasses an allergy vaccine comprising at least one interleukin receptor. Inhibiting the interaction of an interleukin involved in the IgE production pathway (e.g., IL-3, IL-4, IL-5, IL-6, IL-10, IL-13) by immunizing a mammal with an immunogenic interleukin receptor is useful in that, as disclosed herein, antibodies to an interleukin receptor are useful to inhibit interaction of the interleukin receptor with its cognate interleukin ligand thus preventing necessary receptor/ligand interactions in the IgE mediated immune pathway thereby inhibiting or decreasing IgE production.

In particular, it has been discovered that various combinations of interleukin receptors may be administered to a patient afflicted with an allergic disease or condition. Such combinations include: IL-4 receptor and IL-5 receptor; IL-4receptor, IL-5 receptor and IL-13 receptor; IL-4 receptor, IL-5 receptor, IL-13 receptor and IL-3; IL-4 receptor, IL-5 receptor, IL-13 receptor, IL-3 receptor and IL-6 receptor; IL-4 receptor, IL-5 receptor, IL-13 receptor, IL-6 receptor and IL-10 receptor; and IL-3 receptor, IL-4 receptor, IL-5 receptor, IL-13 receptor, IL-6 receptor and IL-10 receptor, to generate an immune response to that receptor.

The invention encompasses administration of each receptor alone. More specifically, the invention includes administering IL-3 receptor alone, IL-4 receptor alone, IL-5 receptor alone, IL-6 receptor alone, IL-10 receptor alone, and IL-13 receptor alone.

The invention includes an allergy vaccine comprising an interferon-alpha, an interferon-alpha receptor, or both. This is because interferon-alpha can exacerbate bronchial asthma attacks (see, e.g., Bini et al., 1999, Mayo Clin. Proc. 74:367–370). Further, administration of interferon-alpha to patients with mild asthma in order to treat other diseases or conditions in the patients resulted in exacerbation of the underlying asthma (Krasnowska et al., 1992, Arch. Immunol. Ther. Exp. (Warsz) 40:75–78). In these patients, the severe asthmatic symptoms resolved upon discontinuation of interferon-alpha, but repeated treatment with interferon-alpha of these same patients several months later resulted in a rapid, more severe exacerbation of the asthma (id.).

These studies suggest that interferon-alpha mediates an allergic, e.g., asthmatic, response in humans such that removal of interferon-alpha and/or inhibiting the interaction of interferon-alpha with its cognate receptor inhibits or decreases an allergic response in a human. Therefore, the present invention encompasses an allergy vaccine that generates an immune response to interferon-alpha, to its receptor, or both, thereby inhibiting the necessary interferon-alpha ligand/receptor interaction required to mediate an allergic response.

The invention further encompasses an allergy vaccine comprising a histamine. One skilled in the art would appreciate, based upon the disclosure provided herein, that inducing an immune response to a histamine associated with the production of IgE prevents interactions between histamine and histamine receptor thereby preventing the development of allergic response in a mammal otherwise mediated by such interactions.

Likewise, the present invention includes an allergy vaccine comprising a histamine receptor, since, as discussed previously herein, an immune response to such a receptor inhibits interactions between histamine and its receptor which would otherwise mediate IgE production. Preventing such interactions inhibits the development of an allergic response mediated by IgE production.

In addition, the present invention encompasses an allergy vaccine comprising at least one leukotriene. Such a vaccine prevents the development of allergic response in a mammal by inhibiting leukotriene/leukotriene receptor interactions necessary for such an allergic response.

Similarly, the present invention includes an allergy vaccine comprising at least one leukotriene receptor since, as stated previously elsewhere herein, induction of an immune response to a leukotriene receptor inhibits the interactions between the leukotriene and its cognate receptor such that the production of IgE dependent on such interactions is also inhibited.

One skilled in the art would appreciate, based upon the disclosure provided herein, that the invention encompasses an allergy vaccine comprising at least one substance described previously (i.e., IgE, interleukin, interferon-alpha, histamine, leukotriene, and receptors thereof) and any combination thereof. Thus, the invention encompasses a wide plethora of combinations as being an allergy vaccine including, but not limited to, an allergy vaccine comprising IgE, IL-4, and IL-10, or an allergy vaccine comprising IL-5 receptor, histamine, a leukotriene receptor, and interferon-alpha. Other combinations as would be understood by one skilled in the art based upon the disclosure provided herein are also included in the present invention.

Further, the afore-mentioned allergy vaccines further comprise a pharmaceutically-acceptable carrier.

In addition, the present invention includes an allergy vaccine further comprising interferon gamma Interferon gamma is useful for the treatment of allergic disease in humans and inhibits many of the effects of IL-4 on both murine and human B cells (see, e.g., King et al., 1989, Proc. Natl. Acad. Sci. USA 86:10085–10089; Snapper, 1996, In: Cytokine Regulation of Humoral Immunity, pp. 324–346, Snapper, ed., John Wiley and Sons, New York; de Vries and Punnonen, Ibid. at pp. 195–215). Therefore, one skilled in the art would appreciate, based upon the disclosure provided herein, that administration of interferon gamma in combination with the administration of at least one of the afore-mentioned substances (i.e., IgE, interleukin, histamine, leukotrienes, and/or their receptors), or any combination thereof, will further treat and/or alleviate an allergic disease or condition by further inhibiting the effect(s) of IL-4 involved in the disease process in the mammal thereby further reducing the level of IgE thus treating and/or alleviating the allergy disease or condition.

DNA-based Allergy Vaccine

One skilled in the art would also appreciate, based upon the disclosure provided herein, that an allergy vaccine (i.e., an immunogenic IgE, IgE receptor, an interleukin involved in IgE production, an interleukin receptor, an interferon-alpha, an interferon-alpha receptor, a histamine, a histamine receptor, a leukotriene, a leukotriene receptor, or any combination thereof) can be administered either as a protein or as a nucleic acid encoding the protein. That is, it is well-known in the art that a nucleic acid encoding an immunogen may be administered as a naked DNA vaccine or may comprise a vector to generate an immune response to the protein encoded by the nucleic acid (Seder and Gurunathan, 1999, New. Eng. J. Med. 341:277–278).

The use of an isolated nucleic acid to generate an immune response, where the nucleic acid is in a vector (e.g., a plasmid or a virus), or where the nucleic acid comprises naked nucleic acid not associated with any other nucleic acid, is well-known in the art. For example, methods for construction of nucleic acid vaccines are described in Burger et al. (1991, J. Gen. Virol. 72:359–367), and are well-known in the art. See also Sambrook et al., 1989, *Molecular Cloning: A Laboratory Manual*, Cold Spring Harbor Laboratory Press, New York; Ausubel et al., 1997, *Current Protocols in Molecular Biology*, Green & Wiley, New York.

Briefly, an isolated nucleic acid encoding, for example, an IgE, an IgE receptor, an interleukin involved in IgE production, and the like, may be administered to a human in a pharmaceutically-acceptable carrier by intramuscular injection or via other routes as described elsewhere herein with respect to the administration of a polypeptide-based allergy vaccine. Additionally, the isolated nucleic acid may comprise a non-live vector such as, but not limited to, plasmid-based recombinants, heat-killed vaccines, liposomes, polyamine derivatives of DNA, and the like, and also viral-based vectors such as for example, but without limitation, adenovirus, poxvirus, herpesvirus, and adenovirus associated vectors.

To express the isolated nucleic acid encoding an allergy vaccine protein, the isolated protein-encoding nucleic acid sequence is operably linked to a promoter/regulatory region capable of driving high levels of expression of the protein in cells. Many such promoter/regulatory sequences are available in the art including, but not limited to, for example, the human cytomegalovirus immediate early promoter/enhancer sequence, the SV40 early promoter, the Rous sarcoma virus promoter and other mammalian promoter/enhancer sequences. Moreover, inducible and tissue specific expression of the isolated nucleic acid operably linked thereto may be accomplished by placing the nucleic acid under the control of an inducible or tissue specific promoter/regulatory sequence. Examples of tissue specific or inducible promoter/regulatory sequences which are useful for this purpose include, but are not limited to the MMTV long terminal repeat (LTR) inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention should be construed to include the use of any promoter/regulatory sequence which is either known or is heretofore unknown, which is capable of driving expression of the nucleic acid operably linked thereto.

Thus, the present invention encompasses an allergy vaccine comprising a nucleic acid encoding at least one of an IgE, an IgE receptor, an interleukin involved in IgE production, an interleukin receptor, an interferon-alpha, an interferon-alpha receptor, a histamine, a histamine receptor, a leukotriene, a leukotriene receptor, or any combination thereof.

Active Immunization Methods

The present invention includes methods of treating an allergy and/or preventing an allergic response in a mammal. The invention encompasses active immunization methods encompassing administering to the mammal an allergy vaccine, i.e., a protein or peptide or the nucleic acid encoding the protein or peptide that elicits an immune response which, in turn, inhibits necessary ligand/receptor interactions required for IgE production. Such allergy vaccines encompass IgE, IgE receptor, an interleukin involved in IgE production (e.g., IL-3, IL-4, IL-5, IL-6, IL-10, IL-13), a receptor for such an interleukin, an interferon-alpha, a histamine, a leukotriene, their respective receptors. Additionally, the present invention encompasses that an allergy vaccine can be administered individually or in combination, either alone or in concert with interferon gamma.

Further, the present invention includes methods of treating an allergy and/or preventing an allergic response comprising administering a nucleic acid encoding IgE, an interleukin involved in IgE production (e.g., IL-3, IL-4, IL-5, IL-6, IL-10, IL-13), an interferon-alpha, a histamine, a leukotriene, and their receptors. The afore-mentioned proteins and/or nucleic acids encoding them can be administered separately or combined, and can be administered separately or in concert with interferon gamma.

The main advantage of the allergy treatment of the invention over prior art treatments is that the present treatment offers long term relief, compared with the relatively short term relief provided by prior art treatments. Further, unlike prior art treatments which are not preventative and which only treat the allergic reaction once it has occurred, the present invention provides a method of prophylaxis that prevents the unwanted immune response. In addition, the present invention provides treatments which circumvent the need for repeated patient compliance. That is, immunization methods do not require ongoing treatment regimens which may make it difficult for patients to properly comply. The lack of need for follow-up and/or ongoing office visits also limits the cost of the treatment as opposed to prior art methods. Moreover, as mentioned previously elsewhere herein, the instant invention circumvents the drawbacks of prior art methods in that unwanted side effects due to the non-specificity of the treatments are reduced or eliminated.

The types of allergy which can be treated using the compositions and methods of the invention include, but are not limited to, asthma, anaphylaxis, hay fever and urticaria. Preferably, the allergy to be treated using the compositions and methods of the invention is asthma.

The present invention further encompasses methods of inhibiting the effect(s) of an interleukin otherwise involved in production of IgE by inhibiting the effect(s) of a substance released by a cell activated by IgE (e.g., histamine and leukotrienes) by active immunization against the substance or its receptor(s) or by passive immunization by administration of an antibody to the substance, an antibody to the receptor(s) of the substance, and/or a soluble receptor of the substance which is not associated with a cell.

One skilled in the art would also appreciate, based upon the disclosure provided herein, that the production of IgE may be further inhibited by administering a cytokine which directly inhibits IgE production in addition to the methods disclosed previously herein. Therefore, the present invention should be construed to include the administration of a cytokine, preferably, IFNγ, IL-12, and the like, which directly inhibits IgE production, in addition to the generation of an immune response to an interleukin involved in IgE production, the administration of an anti-interleukin compound, and/or the administration of an antisense nucleic acid all of which inhibit the production of an interleukin which would otherwise induce IgE production. The IFNγ is administered to a mammal before, at the same time, or after the administration of the immunogenic protein or nucleic acid encoding the same thereby further reducing the production of IgE in the human.

One skilled in the art would appreciate, based upon the disclosure provided herein, that large quantities of these proteins can be produced using a wide variety of methods well-known in the art. For instance, since the amino acid sequences of ILs and their receptors as well as the sequences of the nucleic acids encoding these molecules are known in the art (see, e.g., Snapper, 1996, In: Cytokine Regulation of Humoral Immunity, in passim, Snapper, ed., John Wiley and Sons, New York), large scale purification of ILs and IL-receptor proteins and/or nucleic acids encoding them may be performed according to standard recombinant DNA techniques such as those described, for example, in Sambrook et al. (1989, Molecular Cloning: A Laboratory Manual, Cold Spring Harbor, N.Y.), and in Ausubel et al. (1997, Current Protocols in Molecular Biology, Green & Wiley, New York).

With respect to active immunization, individual or combinations of the proteins (e.g., IgE, interleukins, interferon-alpha, histamines, leukotrienes, and their receptors) can be obtained as described previously elsewhere herein and may be rendered immunogenic using any number of techniques known in the art and described, for example, in Harlow et al. (1999, Using Antibodies: A Laboratory Manual, Cold Spring Harbor Laboratory Press, NY). That is, the allergy vaccine polypeptides disclosed herein for the treatment of allergy are naturally occurring compounds found in the human body. For this reason, simply introducing any one of these compounds into a human may not trigger a humoral or cellular immune reaction. In order to elicit an immune reaction in a human to an IgE, an interleukin, an interferon-alpha, a histamine, a leukotriene, their receptors, and any combination thereof, where administered thereto, it is first necessary that the protein be rendered immunogenic. This may be accomplished in several ways well known in the art of immunogenicity. For example, the protein may be treated with a chemical which induces a modification of the protein which renders the protein immunogenic such as treatment using diazabenzole (Obermyer and Pick, 1903, Wien. Klin. Wschr. 16:659; 1904, Wien. Klin. Wschr. 17:265).

Alternatively, the allergy vaccine protein of interest may be conjugated to another composition, for example, a peptide, a hapten, or gelatin, which renders the interleukin immunogenic. While examples of methods of rendering a protein of interest immunogenic are described herein, the invention should not be construed to be limited to the specific methods disclosed, but rather, should be construed to include any and all known, or heretofore unknown, methods of rendering an interleukin, histamine, leukotriene, IgE, and their receptors, immunogenic.

The protein of interest (e.g., IgE, interleukin, interferon-alpha, histamine, leukotriene, and a receptor thereof) may be rendered immunogenic (and may also be inactivated) by treatment with formalin essentially as described in Carelli et al. (1992, Biomed. and Pharmacother. 46:149–153). Inactivation of a protein normally present in a human for use as an allergy vaccine to be administered to a human, while retaining the immunogenicity of the naturally-occuring protein, has the advantage of preventing the normal action of the introduced protein preventing any side effects which may arise as a result of an excess of the protein in the body. Nonetheless, an immune response, essential for the treatment of the desired allergy, is elicited.

In one aspect, the protein can be treated with formalin using the following protocol. An amount of protein (e.g., about 1 mg) is admixed with about 50 mg of human serum albumin and is dissolved in about 50 ml of sterile 70 mM $Na_2HPO_4$ solution, pH 8.22. The mixture is incubated for six days at about 37° C. after which time it is added to about 8 $\mu l$ of sterile lysine, HCl solution (125 mg/ml). The solution is subsequently dialyzed against about 20 times its volume of sterile PBS solution which is diluted 1:10 (v/v).

The protein may also be rendered immunogenic by conjugation of the interleukin to another composition, for example, bacterial tetanus toxoid protein essentially as described in Chu et al. (1983, Infn. Immun. 40:245–256) and in U.S. Pat. No. 4,902,506.

As is shown in the work of Obermeyer and Pick (1903, Wien. Klin. Wschr. 16:659; 1904, Wien. Klin. Wschr. 17:265), immunization of a mammal with a protein treated with diazabenzole can induce an antibody which has specificity to diazabenzole and specificity to the protein connected to the diazabenzole. Thus, treatment of interleukins and other proteins of interest with diazabenzole can induce antibodies which will react with these interleukins and proteins in an autosystem and an isosystem.

It is not necessary that a full length protein be used as an immunogen in an allergy vaccine for the elicitation of an immune response. Fragments of protein that elicit an immune response which renders the biologically active form of the subject protein inactive are also contemplated by the invention. Fragments of protein may be obtained by degradation of full length molecule, by chemical synthesis, or by cloning and expression of such fragments using molecular biology technology described, for example, in Sambrook et al. (1989, Molecular Cloning. A Laboratory Manual, Cold Spring Harbor, N.Y.), and in Ausubel et al. (1997, Current Protocols in Molecular Biology, Green & Wiley, New York). Once the DNA encoding the interleukin is known, it is a simple matter to obtain fragments of the interleukin by subcloning and expressing DNA encoding a fragment of the interleukin.

Modifications of the protein (e.g., IgE, interleukin, interferon-alpha, histamine, leukotriene, and their receptors), or a fragment thereof, may be made by direct modification of the protein or fragment thereof. It will be appreciated, of course, that a peptide may incorporate amino acid residues which are modified without affecting activity (e.g., the immunogenicity of the protein). For example, the terminal portion of the peptide may be derivatized to include blocking groups, i.e., chemical substituents suitable to protect and/or stabilize the N- and C-termini from "undesirable degradation", a term meant to encompass any type of enzymatic, chemical or biochemical breakdown of the compound at its termini which is likely to affect the function of the compound as an immunogenic agent, i.e., sequential degradation of the interleukin at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketoneforming alkyl groups, particularly lower alkyl groups such as methyl, ethyl and propyl, and amide-forming amino groups such as primary amines (—NH$_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it Further, it will be appreciated that the free amino and carboxyl groups at the termini can be removed altogether from the peptide to yield desamino and descarboxylated forms thereof without affect on peptide activity.

Other modifications can also be incorporated without adversely affecting immunogenic activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicylic and the like, to provide a water soluble salt of the peptide is suitable for use as an immunogenic agent.

The present invention also provides for analogs of proteins or peptides of interleukins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of peptides, e.g., acetylation, or carboxylation. Also included are modifications of glycosylation, e.g., those made by modifying the glycosylation patterns of a peptide during its synthesis and processing or in further processing steps; e.g., by exposing the peptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

As described herein, also included are proteins and peptides which have been modified using ordinary molecular biological techniques so as to improve their resistance to proteolytic degradation or to optimize solubility properties or to render them more suitable as an immunogenic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

Further, one skilled in the art would appreciate, based upon the disclosure provided herein, that the invention encompasses proteins and fragments and portions thereof where the portion or fragment elicits an immune response which blocks the activity of the naturally occurring, i.e., native, protein. Therefore, the invention encompasses full-length proteins, peptides, and also fragments and/or portions thereof, that induce an immune response that in turn, inhibits IgE production.

An allergy vaccine can comprise a sterile solution of modified interleukins, histamine, leukotrienes and IgE, and/or their receptors, dissolved in 0.9% sodium chloride or sterile water. Final concentration of interleukins, leukotrienes, histamine, IgE, and/or their receptors, is 100–200 micrograms/ml. Preferably, allergy vaccines are administered intramuscularly or subcutaneously at dosages between 200and 500 micrograms once a week for 3 to 4 weeks, then once a month for 3 additional months. Other schedules are possible such that more or less frequent immunizations can be administered over longer periods of time.

Typically, first immunization is given without an adjuvant, and subsequent doses are administered with adjuvants. Based on clinical response and immunologic parameters (e.g., antibody titers, avidity of antibodies, antibody isotypes, and the like), further booster immunizations can be administered as deemed necessary.

Briefly, active immunization using interleukins can be performed as follows. The initial titer of IgE is assessed. A high level of IgE is a marker of risk for allergy. Thus, a mammal exhibiting high titers of IgE will be treated to prevent allergy.

The immunogen of choice (i.e., IgE, IgE-receptor, I L-3, IL-5, IL-6, IL-10, IL-13, receptor to IL-3, IL-5, IL-6, IL-10, IL-13, interferon-alpha, interferon-alpha receptor, histamine, histamine receptor, leukotriene, leukotriene receptor) can be administered approximately 2–3 times/month.

In one aspect, IL-4 is administered alone or in combination with other interleukins (e.g., IL-3, IL-5, IL-6, IL-10, and IL-13). Each interleukin is administered at a dosage ranging from about 100 to 1000 micrograms per dose. Preferably, the first dose is administered without adjuvant, but later doses are administered with adjuvant.

After the third injection, the level of, for instance, interleukins and IgE is assessed. Upon assessment, if improvement (e.g., IgE level decreases and/or the level of interleukin IL-4 and IL-5, and IL-13, or at least IL-4 and IL-5, decreases) is detected along with clinical improvement, then interleukin vaccinations continue to be administered approximately once per month for 3 months at a dose of approximately 500 micrograms per injection.

If no improvement is detected according to standard laboratory assay and/or well-known clinical indices, interleukins are administered (IL-3, IL-6, IL-10) at a dose about 500 micrograms per injection.

If still no improvement is detected, i.e., in difficult cases, vaccination is performed using interleukins and interferon gamma (not treated by formalin or made immunogenic by other methods), at a dosage between about $1 \times 10^4$ to $1 \times 10^8$ units per square meter of body surface area.

The immune response to the immunogenic interleukin is measured by standard immunological techniques such as ELISA or Western blotting and other such techniques well-known in the art or to be developed in the future. A variety of immunoassay formats may be used to select antibodies specifically immunoreactive with a particular protein. See, e.g., Harlow et al. (1999, Using Antibodies: A Laboratory Manual, Cold Spring Harbor Laboratory Press, NY) for a description of immunoassay formats and conditions that can be used to determine specific immunoreactivity.

In another aspect, IL-4 is administered in combination with another interleukin involved in IgE production, and/or in combination with one or more proteins selected from the group consisting of IgE, IgE receptor, interleukin receptor, interferon-alpha, interferon-alpha receptor, histamine, histamine receptor, leukotriene, and leukotriene receptor, in any combination.

In addition, the instant invention includes methods of treating or preventing asthma, allergy, and autoimmune conditions comprising administering interferon gamma.

Passive Immunization Methods

In addition to the active immunization methods disclosed previously elsewhere herein, the present invention includes methods of treating an allergy and/or preventing an allergic response in a mammal comprising passively administering a protein (i.e., an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor) that directly inhibits IgE production without generating an immune response thereto.

The present invention does not encompass administering an anti-IL-4 where the antibody is administered alone or with another antibody that specifically binds with IL-4 even if the antibodies recognize different epitopes present in the IL-4 molecule.

Similarly, the present invention does not encompass administering an anti-IL-5 where the antibody is administered alone or with another antibody that specifically binds with IL-5 even if the antibodies recognize different epitopes present in the IL-5 molecule.

Nevertheless, the present invention includes administering anti-IL-4, anti-IL-5 antibody, alone or combined, in addition to administering at least one protein selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha, an anti-histamine antibody, an anti-histamine receptor antibody, a soluble histamine receptor, an anti-leukotriene antibody, an anti-leukotriene receptor antibody, and a soluble leukotriene receptor. Thus, the invention includes administering anti-IL-4 and anti-IL-5, either separately or combined, in combination with one or more of the afore-mentioned proteins, or a fragment thereof.

The present invention includes passive immunization comprising administering an anti-interleukin antibody where the interleukin is involved in IgE production (e.g., IL-3, IL-4, IL-5, IL-6, IL-10, IL-13) together with another ingredient that inhibits a receptor-ligand interaction involved in IgE production (e.g., an anti-IgE antibody, an anti-IgE receptor antibody, a soluble IgE receptor, an anti-interleukin receptor antibody, a soluble interleukin receptor, an anti-interferon-alpha antibody, an anti-interferon alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor).

The present invention also encompasses a passive immunization method comprising administering an antisense nucleic acid complementary to a nucleic acid encoding IgE, an interleukin involved in IgE production (e.g., IL-3, IL-4, IL-5, IL-6, IL-10, IL-13), an interferon-alpha, a histamine, a leukotriene, and/or an antisense nucleic acid complementary to a nucleic acid encoding their respective receptors.

The invention encompasses administering any or all of these substances either alone or combined.

Further, the invention encompasses administering interferon gamma in concert with at least one of the above-mentioned substances for passive immunization purposes.

Proteins

In addition to the active immunization methods disclosed previously elsewhere herein, the invention includes passive immunization methods of inhibiting the action of IgE by administering to a mammal antibodies to IgE, antibodies to IgE receptor, and soluble IgE receptor. Further, in addition to such passive immunization, the invention includes administering to a mammal antibodies to an interleukin receptor where the interleukin mediates production of IgE (e.g., IL-3, IL-4, IL-5, IL-6, IL-10, IL-13), or soluble interleukin receptor thereby preventing, treating, or both, the development of allergic response in a mammal.

The invention further includes methods of inhibiting the action of interferon-alpha by administering to a mammal antibodies to interferon-alpha, antibodies to interferon-alpha receptor, and soluble interferon-alpha receptor.

Additionally, the invention includes a method of inhibiting the action of histamine by administering to a mammal antibodies to histamine, antibodies to histamine receptor, and soluble histamine receptor.

Furthermore, the invention includes a method of inhibiting the action of leukotrienes by administering to a mammal antibodies to leukotrines, antibodies to leukotriene receptor, and soluble leukotriene receptor.

One skilled in the art would appreciate, based upon the disclosure provided herein, that the invention encompasses proteins, peptides, and fragments or portions thereof, which when administered, inhibit production of IgE. That is, the invention is not limited to passive immunization using the full-length protein. The invention also encompasses any portion or fragment of a protein involved in IgE production (e.g., IgE, interleukins IL-3, IL-4, IL-5, IL-6, IL-10, and IL-13, interferon-alpha, histamine, leukotriene, and their receptors, and/or antibodies thereto) that is capable of blocking a ligand/receptor interaction involved in IgE production.

The decision to use active or passive immunization is one which will be made by the skilled artisan and will depend upon any number of factors including, but not limited to, the type of allergy being treated, the severity of the disease and the age and overall health of the individual being treated.

Further, the invention includes passive immunization of patients with plasma or IgG from donors immunized with receptors to IL-3, IL-4, IL-5, IL-6, IL-10, and IL-13. The invention also includes passive immunization of patients with plasma or IgG from donors immunized with naturally occurring substances typically present in the human body which have been treated to render them more immunogenic (e.g., IgE, histamine, leukotrienes, and their respective receptors), either with or without administration of interferon gamma.

The present invention encompasses passive immunization by administering plasma and/or IgG from donors immunized with an interleukin involved in IgE production (e.g., IL-3, IL-4, IL-5, IL-6, IL-10, and IL-13), in combination with plasma and/or IgG from a donor immunized with a different interleukin involved in IgE production.

Further, the invention encompasses administering plasma and/or IgG from donors immunized with at least one interleukin involved in IgE production (e.g., IL-3, IL-4, IL-5, IL-6, IL-10, and IL-13) which donors were also immunized with at least one protein, or fragment thereof, selected from the group consisting of IgE, IgE receptor, an interleukin receptor, an interferon-alpha, an interferon-alpha receptor, a histamine, a histamine receptor, a leukotriene, and a leukotriene receptor.

These methods of passive immunization not directly involving the generation of an immune response in a mammal may be particularly useful to treat an IgE-mediated immune response where it is not possible to generate an anti-interleukin immune response. Further, such methods are also useful to treat immunosuppressed individuals who may be unable to mount a sufficient immune response to the interleukin involved in IgE production.

Thus, the present invention should be construed to encompass methods for inhibiting the effect(s) of an interleukin otherwise involved in production of IgE (e.g., IL-3, IL-4, IL-5, IL-6, IL-10, IL-13) such that IgE production is inhibited or diminished by passive immunization by administration of an anti-interleukin compound (e.g., an antibody to the interleukin receptor, or a soluble receptor not associated with a cell) or by suppressing production of the interleukin or its receptor using antisense nucleic acids.

With respect to passive immunization using antibodies, antibodies which are directed against any of the aforementioned substances may be administered to a mammal in order to reduce production of IgE in the patient. The types of antibodies which may be used include polyclonal antibodies, monoclonal antibodies, phage-derived antibodies, synthetic antibodies, humanized antibodies, and the like. As noted herein, antibody technology is described, for example, in Harlow et al. (1999, supra). Polyclonal antibodies directed against an interleukin protein may be made by immunizing any suitable animal and obtaining immune serum from the animal at selected intervals following immunization.

Monoclonal antibodies directed against full length or peptide fragments of a protein of interest may be prepared using any well known monoclonal antibody preparation procedures, such as those described, for example, in Harlow et al. (supra). Quantities of the desired peptide may also be synthesized using chemical synthesis technology. Alternatively, DNA encoding the desired peptide may be cloned and expressed from an appropriate promoter/regulatory sequence in cells which are suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125–168), and the references cited therein. Further, the antibody may be "humanized" using the technology described in Wright et al., (supra) and in the references cited therein.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning. A Laboratory Manual, Cold Spring Harbor, N.Y.) and in Ausubel et al. (Ausubel et al., 1993, Current Protocols in Molecular Biology, Green & Wiley, New York).

Bacteriophage which encode the desired antibody may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The invention thus includes an isolated DNA encoding an anti-interleukin antibody or DNA encoding a portion of the antibody.

To isolate DNA encoding an antibody, for example, DNA is extracted from antibody expressing phage obtained as described herein. Such extraction techniques are well known in the art and are described, for example, in Sambrook et al. (supra) and in Ausubel et al. (supra).

Another form of antibody includes a nucleic acid sequence which encodes the antibody and which is operably linked to promoter/regulatory sequences which can direct expression of the antibody in vivo. For a discussion of this technology, see, for example, Cohen (1993, Science 259:1691–1692), Fynan et al. (1993, Proc. Natl. Acad. Sci. 90:11478–11482) and Wolff et al. (1991, Biotechniques 11:474–485) which describe the use of naked DNA as an antibody/vaccine. For example, a plasmid containing suitable promoter/regulatory sequences operably linked to a DNA sequence encoding an antibody may be directly administered to a patient using the technology described in the aforementioned references.

Alternatively, the promoter/enhancer sequence operably linked to DNA encoding the antibody may be contained within a vector, which vector is administered to the patient. The vector may be a viral vector which is suitable as a delivery vehicle for delivery of the DNA encoding the antibody to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. USA 94:12744–12746). Examples of viral vectors include, but are not limited to, a recombinant vaccinia virus, a recombinant adenovirus, a recombinant retrovirus, a recombinant adeno-associated virus, a recombinant avian poxvirus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

The identity, selection and means for obtaining a desired antibody useful for treatment or prevention of an allergic disease may be performed by the skilled artisan using conventional technology when in possession of the present invention.

Other anti-interleukin compounds may include, but are not limited to, isolated proteins and isolated peptides and isolated nucleic acid sequences encoding receptors for the desired interleukin, which when administered to the human, serve to block binding of the endogenous interleukin to its cognate receptor on a cell, thereby inhibiting the action of the endogenous interleukin. Isolated proteins and peptides having interleukin receptor activity, and isolated nucleic acids encoding the same, may be chemically synthesized by conventional methods known in the art, or they may be purchased from a commercial source if available. In one embodiment of the invention, the interleukin receptor, being a protein, a peptide or as used herein, a nucleic acid encoding the same, may be produced using recombinant techniques in vitro in sufficiently large quantities for use in a therapeutic composition for use in treating or preventing an allergic disease. In addition, a recombinant virus vector comprising DNA encoding the desired interleukin receptor may be prepared using conventional recombinant DNA technology procedures.

The interleukin receptor, or the antibody to the interleukin receptor of the invention (collectively referred to herein as an "anti-interleukin compound"), can be formulated in a pharmaceutical composition which is suitable for administration of the compound to a human patient. It will be appreciated that the precise formulation and dosage amounts will vary depending upon any number of factors, including, but not limited to, the type and severity of the disease to be treated, the route of administration, the age and overall health of the individual, the nature of the anti-interleukin compound, etc. However, the preparation of a pharmaceutically acceptable composition having an appropriate pH, isotonicity, stability and other characteristics is within the skill of the art. Pharmaceutical compositions are described in the art, for example, in Remington's Pharmaceutical Sciences (Genaro ed., 1985, Mack Publishing Co., Easton, Pa.).

The amount of the anti-interleukin compound administered, whether it is administered as protein or as nucleic acid, is sufficient to prevent, diminish or alleviate the allergic state. The pharmaceutical compositions useful for practicing the invention may be administered to deliver a dose of between about 1 ng/kg and about 100 mg/kg of patient body weight. Suitable amounts of the anti-interleukin compound for administration include doses which are high enough to have the desired effect without concomitant adverse effects. When the anti-interleukin compound is a protein or peptide, a preferred dosage range is from about 10 to about 1000 µg of protein or peptide per kg of patient body weight. When the anti-interleukin compound is administered in the form of DNA encoding the same contained within a recombinant virus vector, a dosage of between about $10^2$ and about $10^{11}$ plaque forming units of virus per kg of patient body weight may be used. When naked DNA encoding the anti-interleukin compound is to be administered as the pharmaceutical composition, a dosage of between about 10 µg about several mg of DNA per kg of patient body weight may be used.

In the practice of the methods of the invention, a composition containing an anti-interleukin compound is administered to a patient in a sufficient amount to prevent, diminish or alleviate an asthmatic state in the individual. Patients to be treated include children and adults who have atopic allergy. In particular, patients to be treated include those who have atopic asthma.

The frequency of administration of an anti-interleukin compound to a patient will also vary depending on several factors including, but not limited to, the type and severity of the allergy to be treated, the route of administration, the age and overall health of the individual, the nature of the anti-interleukin compound, etc. It is contemplated that the frequency of administration of the anti-interleukin compound to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate anti-interleukin compound, these pharmaceutical compositions may contain pharmaceutically-acceptable carriers and other ingredients known to enhance and facilitate drug administration. Thus, such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to admininster the appropriate anti-interleukin compound to a patient according to the methods of the invention. Oral delivery of antibodies is described in Reilly et al. (1997, Clin. Pharmacol. 32:313–323).

In the case of treatment of asthma, the composition of the invention is preferably administered to the human by a lung inhalation route, i.e., via a nebulizer or other lung inhalation device.

An anti-interleukin compound may be administered in conjunction with other compounds which are used to treat asthma. Such compounds include, but are not limited to, corticosteroids, sodium cromolyn, methylxanthines, leukotriene pathway modifiers, anti-cholinergic agents, and rapid relief medications that counteract bronchospasm, e.g., primarily beta-adrenergic agents. The choice of which additional compound to administer will vary depending upon any number of the same types of factors that govern the selection of dosage and administration frequency of the anti-interleukin compound. Selection of these types of compounds for use in conjunction with an anti-interleukin compound for practice of the method of the invention is well within the skill of those in the art.

The invention encompasses use of interferon gamma as both a therapeutic agent to treat asthma and as a preventative agent to prevent asthma attacks. Thus, interferon gamma can be used in both instances. Interferon gamma can be administered in doses ranging from about $10^4$ to $10^6$ units per square meter of body surface area Further, interferon gamma is administered before, along with, or after administration of IgE, IgE receptor, interleukin, interleukin receptor, interferon-alpha, interferon-alpha receptor, histamine, histamine receptor, leukotriene, leukotriene receptor (i.e., active immunization) and/or antibodies to any or all of the preceding substances excluding anti-interleukin antibodies (i.e., passive immunization). The invention encompasses administration of any of these substances alone, together, or in any combination thereof, either with or without interferon gamma.

Antisense Molecules

The invention also includes a method of preventing an allergic response in a human comprising administering an antisense nucleic acid complementary to a nucleic acid encoding at least one of IgE, an interleukin involved in IgE production such as IL-3, IL-4, IL-5, IL-6, IL-10, and IL-13, an interferon-alpha, a histamine, and a leukotriene. One skilled in the art would appreciate, based upon the disclosure provided herein, that inhibiting expression of a nucleic acid encoding a substance involved in IgE production causes a reduction in the production of IgE which, in turn, prevents an allergic response. In this regard, certain molecules, including antisense nucleic acids and ribozymes, are useful in inhibiting expression of a nucleic acid complementary thereto.

Similarly, one skilled in the art would appreciate, based upon the disclosure provided herein, that the administration of an antisense nucleic acid complementary to a nucleic acid encoding a receptor for IgE, an interleukin involved in IgE production such as IL-3, IL-4, IL-5, IL-6, IL-10, and IL-13, an interferon-alpha, a histamine, and a leukotriene would also inhibit IgE production thereby treating and/or preventing an allergic immune response. That is, inhibition of production of a receptor prevents the ligand/receptor interaction(s) required for induction of IgE synthesis from taking place. Thus, inhibition of expression of a receptor involved in induction of IgE production reduces IgE biosynthesis and prevents and/or treats an allergic response mediated by IgE.

In one aspect, the invention includes a method of inhibiting the production of at least one of IgE, an interleukin involved in IgE production, an interferon-alpha, a histamine, and a leukotriene by administering to a mammal an antisense nucleic acid complementary to a nucleic acid encoding the protein. Thus, by inhibiting the expression of the protein which would otherwise be involved in increasing production of IgE, the antisense nucleic acid inhibits the production of IgE and also treats and/or prevents an allergic response.

Additionally, the invention includes a method of inhibiting the production of IgE by administering to a mammal an antisense nucleic acid complementary to a nucleic acid encoding a receptor for IgE, an interleukin involved in IgE production, an interferon-alpha, a histamine, and a leukotriene. Therefore, the invention encompasses inhibiting the expression of a receptor involved in IgE production thereby inhibiting the requisite ligand/receptor interaction(s) necessary for the induction of IgE production. As disclosed previously elsewhere herein, inhibition of IgE production prevents and/or treats an allergic response driven by IgE production such as, but not limited to, asthma.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura, 1988, Anal. Biochem. 172:289. Such antisense molecules may be provided to the cell via genetic expression using DNA encoding the antisense molecule as taught by Inoue, 1993, U.S. Pat. No. 5,190,931 (incorporated by reference herein in its entirety).

Alternatively, antisense molecules of the invention may be made synthetically and then provided to a human or veterinary patient. Antisense oligomers of about 15 nucleotides are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

In addition to using an antisense molecule to inhibit expression of a nucleic acid encoding an interleukin or an interleukin receptor, the present invention encompasses the use of ribozymes in this manner. Ribozymes are another nucleic acid that may be transfected into a cell to inhibit nucleic acid expression in the cell. Ribozymes and their use for inhibiting gene expression are also well known in the art (see, e.g., Cech et al., 1992, J. Biol. Chem.

267:17479–17482; Hampel et al., 1989, Biochemistry 28:4929–4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of the proteins of interest may be designed by incorporating target sequences into the basic ribozyme structure which are complementary to the mRNA sequence of the nucleic acid encoding the protein of interest. Ribozymes targeting an interleukin involved in IgE production may be synthesized using commercially available reagents (Applied Biosystems, Inc., Foster City, Calif.) or they may be expressed from DNA encoding them.

Compounds that inhibit expression of a nucleic acid encoding an interleukin involved in IgE production and/or encoding its receptor, i.e., antisense and ribozyme molecules, are administered to a human as described elsewhere herein for the delivery of nucleic acids generally.

In addition, the instant invention includes methods of treating or preventing asthma, allergy, and autoimmune conditions comprising administering interferon-gamma (IFNγ).

Active and Passive Methods Combined

One skilled in the art would appreciate, based upon the disclosure provided herein, that the above-disclosed allergy methods of active and passive immunization can be combined to effect treatment and/or prevention of asthma, and allergic and autoimmune conditions. Thus, the invention encompasses active/passive immunization with at least one of: an interleukin involved in IgE production, a receptor of such an interleukin, an anti-interleukin receptor antibody, an interferon-alpha, an interferon-alpha receptor, an anti-interferon-alpha antibody, an anti-interferon alpha receptor antibody, a soluble interferon-alpha receptor, histamine, histamine receptor, anti-histamine antibody, anti-histamine receptor antibody, leukotriene, leukotriene receptor, anti-leukotriene antibody, anti-leukotriene receptor antibody, IgE, IgE receptor, anti-IgE antibody, and anti-IgE receptor antibody, and any combination of these substances.

This is because as disclosed herein, any decrease in the interaction between IgE and its receptor and/or any decrease in the interaction of the substances released by cells activated by binding of IgE (e.g., histamine, leukotrienes) with their receptors (e.g., histamine receptor and leukotriene receptor) alleviates, prevents, or treats asthma, and other allergic and autoimmune conditions mediated by IgE and substances produced upon stimulation by IgE. Therefore, methods that inhibit the release of IgE and/or its action, including methods that inhibit, among other things, IgE binding with its receptor, binding of various interleukins with their receptors, binding of interferon-alpha with its cognate receptor, and interaction of histamine and leukotrienes with their respective receptors, all prevent, treat, or both, asthma, allergies, and autoimmune conditions mediated by such interactions.

In addition, the various methods, both passive and active immunization using proteins or nucleic acid encoding protein, can be combined with methods of treating or preventing asthma, allergy, and autoimmune conditions comprising administering interferon gamma.

Further, with regard to passive immunization by administering an antibody that specifically binds with an interleukin involved in IgE production, the antibody to the interleukin is not administered alone or in combination with another antibody to the same or a different interleukin involved in IgE production. Instead, with regard to passive immunization using antibodies directed to interleukins involved in IgE production, an antibody to an interleukin involved in IgE production is administered in combination with at least one other protein selected from the following group: a soluble receptor of such an interleukin, an anti-interleukin receptor antibody, an interferon-alpha receptor, an anti-interferon-alpha antibody, an anti-interferon alpha receptor antibody, an anti-histamine antibody, an anti-histamine receptor antibody, a histamine receptor, a leukotriene receptor, an anti-leukotriene antibody, anti-leukotriene receptor antibody, an IgE receptor, an anti-IgE antibody, and anti-IgE receptor antibody, and any combination of these substances.

Kits

The invention includes various kits comprising at least one substance (e.g., IgE, an interleukin involved in IgE production, an interferon-alpha, a histamine, a leukotriene, and their respective receptors) that when administered either as a protein or as a nucleic acid encoding the protein, generate an immune response such that the necessary ligand/receptor interaction is blocked and IgE production is inhibited thereby. The kits further comprise an applicator and instructional materials which describe use of the compound to perform the methods of the invention.

The invention also includes various kits comprising at least one substance (e.g., an anti-IgE antibody, a soluble IgE receptor, an anti-IgE receptor antibody, a soluble receptor for an interleukin involved in IgE production, an anti-interleukin receptor antibody, an anti-interferon-alpha antibody, an anti-interferon-alpha receptor antibody, a soluble interferon-alpha receptor, an anti-histamine antibody, a soluble histamine receptor, an anti-histamine receptor antibody, an anti-leukotriene antibody, a soluble leukotriene receptor, and an anti-leukotriene receptor antibody) that inhibits production of IgE when administered to a mammal without the need to generate an immune response in the animal although an immune response may be generated.

The invention encompasses kits comprising at least one antisense nucleic acid complementary to a nucleic acid encoding at least one IgE, IgE receptor, interleukin involved in IgE production, a receptor of such an interleukin, an interferon-alpha, an interferon-alpha receptor, a histamine, a histamine receptor, a leukotriene, and a leukotriene receptor. Administration of such an antisense nucleic acid inhibits expression of the protein thereby inhibiting the ligand/ receptor interaction required for IgE production in which the protein would otherwise participate. Inhibiting the requisite ligand/receptor interaction, in turn, inhibits production of IgE thereby inhibiting allergic responses mediated thereby.

The kits further comprise and applicator and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for preventing an allergic response in a mammal. The kit is used pursuant to the methods disclosed in the invention. Briefly, the kit may be used to administer an allergy vaccine comprising at least one of IgE, an interleukin involved in the production of IgE, an interferon-alpha, a histamine, a leukotriene, and a receptor of these proteins. The allergy vaccine may be introduced as a protein, or fragment thereof, or as an isolated nucleic acid encoding a protein, or portion thereof, into a mammal in order to decrease the level of the interleukin in the mammal thereby reducing the level of IgE in the mammal which, in turn, prevents the allergic response in the mammal.

The kit further comprises an applicator useful for administering the protein and/or nucleic acid encoding the protein to the mammal. The particular applicator included in the kit will depend on the method used to administer the protein and/or the nucleic acid encoding the same to the mammal, and such applicators are well-known in the art and may include, among other things, a pipette, a syringe, a dropper, a spray, an inhaler, a nebulizer, an endotracheal tube, a bronchoscope, and the like. Moreover, the kit comprises an instructional material for the use of the kit. These instructions simply embody the disclosure provided herein.

In another aspect, the kit includes interferon gamma. The interferon gamma is administered pursuant to the methods disclosed herein. Briefly, interferon gamma is known to inhibit the production and/or effects of IL-4 including the production of IgE. Therefore, interferon gamma effects a further reduction in IgE level thereby preventing an allergic response in the human.

The invention includes a kit for treating an allergy in a mammal. The kit is used pursuant to the methods disclosed in the invention. Briefly, the kit comprises and may be used to administer at least one of a soluble IgE receptor, an anti-IgE receptor antibody, a soluble receptor for an interleukin involved in IgE production (e.g., IL-3, IL-4, IL-5, IL-6, IL-10, and IL-13), an anti-interleukin receptor antibody, an anti-interferon-alpha antibody, an anti-interferon-alpha receptor antibody, a soluble interferon-alpha receptor, an anti-histamine antibody, a soluble histamine receptor, an anti-histamine receptor antibody, an anti-leukotriene antibody, a soluble leukotriene receptor, and an anti-leukotriene receptor antibody. The substance may be administered to the mammal as a protein, or fragment thereof, or as an isolated nucleic acid encoding a protein, or portion thereof, in order to block the ligand/receptor interactions required for IgE production thereby reducing the level of IgE produced in the mammal which, in turn, prevents the allergic response in the mammal.

The kit further comprises an applicator useful for administering the protein and/or nucleic acid encoding the protein to the mammal. The particular applicator included in the kit will depend on the method used to administer the interleukin and/or the nucleic acid encoding same to the mammal and such applicators are well-known in the art and may include, among other things, a pipette, a syringe, a dropper, a spray, an inhaler, a nebulizer, an endotracheal tube, a bronchoscope, and the like. Moreover, the kit comprises an instructional material for the use of the kit. These instructions simply embody the disclosure provided herein.

In another aspect, the kit includes interferon gamma. The interferon gamma is administered pursuant to the methods disclosed herein. Briefly, interferon gamma is known to inhibit the production and/or effects of IL-4 including the production of IgE. Therefore, interferon gamma effects a further reduction in IgE level thereby preventing an allergic response in the human.

The invention includes a kit for treating an allergy in a mammal. The kit is used pursuant to the methods disclosed in the invention. Briefly, the kit comprises and may be used to administer at least one anti-interleukin antibody where the interleukin is involved in IgE production (e.g., IL-3, IL-4, IL-5, IL-6, IL-10, and IL-13) in combination with a second protein selected from the group consisting of a soluble IgE receptor, an anti-IgE receptor antibody, a soluble receptor for an interleukin involved in IgE production (e.g., IL-3, IL-4, IL-5, IL-6, IL-10, and IL-13), an anti-interleukin receptor antibody, an anti-interferon-alpha antibody, an anti-interferon-alpha receptor antibody, a soluble interferon-alpha receptor, an anti-histamine antibody, a soluble histamine receptor, an anti-histamine receptor antibody, an anti-leukotriene antibody, a soluble leukotriene receptor, and an anti-leukotriene receptor antibody. The proteins can be administered to the mammal as a protein, or fragment thereof, or as an isolated nucleic acid encoding a protein, or portion thereof, in order to block the ligand/receptor interactions required for IgE production thereby reducing the level of IgE produced in the mammal which, in turn, prevents the allergic response in the mammal.

The kit further comprises an applicator useful for administering the protein and/or nucleic acid encoding the protein to the mammal. The particular applicator included in the kit will depend on the method used to administer the interleukin and/or the nucleic acid encoding same to the mammal and such applicators are well-known in the art and may include, among other things, a pipette, a syringe, a dropper, a spray, an inhaler, a nebulizer, an endotracheal tube, a bronchoscope, and the like. Moreover, the kit comprises an instructional material for the use of the kit. These instructions simply embody the disclosure provided herein.

In another aspect, the kit includes interferon gamma. The interferon gamma is administered pursuant to the methods disclosed herein. Briefly, interferon gamma is known to inhibit the production and/or effects of IL-4 including the production of IgE. Therefore, interferon gamma effects a further reduction in IgE level thereby preventing an allergic response in the human.

The invention further includes a kit for treating an allergy in a mammal. The kit is used pursuant to the methods disclosed in the invention. Briefly, the kit comprises and may be used to administer an antisense nucleic acid complementary to a nucleic acid encoding IgE, IgE receptor, an interleukin involved in the production of IgE (e.g., IL-3, IL-4, IL-5, IL-6, IL-10, and IL-13), an interleukin receptor, an interferon-alpha, an interferon-alpha receptor, a histamine, a histamine receptor, a leukotriene, and a leukotriene receptor. The antisense nucleic acid inhibits expression of nucleic acid to which it is complementary thereby inhibiting production of the protein encoded thereby. The reduction in expression of the protein in turn inhibits the ligand/receptor interactions necessary for production of IgE by decreasing the amount of protein available to participate in such interactions. Decreasing the level of IgE in the mammal, in turn, treats the allergy in the mammal.

The kit further comprises an applicator useful for administering the antisense nucleic acid to the mammal pursuant to the methods disclosed elsewhere herein. The particular applicator included in the kit will depend on the method used to administer the antisense nucleic acid to the mammal and such applicators are well-known in the art and may include, among other things, a pipette, a syringe, a dropper, a nebulizer, an endotracheal tube, a bronchoscope, and the like. Moreover, the kit comprises an instructional material for the use of the kit. These instructions simply embody the disclosure provided herein.

In one aspect, the kit comprises interferon gamma which is administered pursuant to the methods disclosed elsewhere herein.

The invention encompasses a kit for preventing an allergic response in a mammal. The kit is used pursuant to the methods disclosed in the invention. Briefly, the kit can be used to administer a pharmaceutical composition where the composition comprises at least one allergy vaccine in an amount effective for preventing an allergic response in a mammal. The pharmaceutical composition also comprises a pharmaceutically acceptable carrier.

As stated previously elsewhere herein, the allergy vaccine comprises a protein selected from the group consisting of IgE, an IgE receptor, an interleukin involved in the production of IgE, a receptor for an interleukin involved in the production of IgE, an interferon-alpha, an interferon-alpha receptor, a histamine, a histamine receptor, a leukotriene, and a leukotriene receptor.

The kit further encompasses an applicator, and an instructional material for the use thereof in accordance with the methods disclosed elsewhere herein.

The allergy vaccine comprised by the pharmaceutical composition can be introduced as a protein, peptide, or a fragment thereof, or as an isolated nucleic acid encoding a protein, peptide or fragment thereof, in order to inhibit the ligand/receptor interactions that mediate IgE production thereby inhibiting production of IgE thus preventing an allergic response mediated by IgE.

In one aspect, the kit further comprises interferon gamma.

The invention further includes a kit for treating an allergy in a mammal. The kit comprises a pharmaceutical composition comprising at least one protein in an amount effective for treating an allergy in a mammal. The pharmaceutical composition further comprises a pharmaceutically acceptable carrier.

The protein is selected from an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor, wherein the interleukin is at least one interleukin involved in the production of IgE in a mammal.

The kit comprises an applicator, and an instructional material for the use of the kit in accordance with the methods disclosed elsewhere herein.

In one aspect, the kit further comprises interferon gamma.

The invention includes a kit for treating an allergy in a mammal. The kit comprises a pharmaceutical composition comprising an antisense nucleic acid in an amount effective for treating an allergy in a mammal. The antisense nucleic acid is complementary to a nucleic acid encoding at least one ingredient selected from the group consisting of IgE, an IgE receptor, an interleukin involved in the production of IgE in a mammal, a receptor to an interleukin involved in the production of IgE in a mammal, an interferon-alpha, an interferon-alpha receptor, a histamine, a histamine receptor, a leukotriene, and a leukotriene receptor. Moreover, the pharmaceutical composition further comprises a pharmaceutically acceptable carrier.

The kit comprises an applicator, and an instructional material for the use thereof to inhibit production of IgE thereby treating an allergy in a mammal.

In another aspect, the kit further comprises interferon gamma.

The invention includes a pharmaceutical composition comprising at least one protein selected from the group consisting of an IgE, an IgE receptor, an interleukin involved in production of IgE in a mammal, a receptor for an interleukin involved in production of IgE in a mammal, an interferon-alpha, an interferon-alpha receptor, a histamine, a histamine receptor, a leukotriene, a leukotriene receptor. The protein is in an in an amount effective for preventing an allergic response in a mammal. Such amount can be readily determined based upon the teachings disclosed herein. Further, the composition comprises a pharmaceutically-acceptable carrier.

The invention includes a pharmaceutical composition comprising at least one isolated nucleic acid encoding a protein selected from the group consisting of an IgE, an IgE receptor, an interleukin involved in production of IgE in a mammal, a receptor for an interleukin involved in production of IgE in a mammal, an interferon-alpha, an interferon-alpha receptor, a histamine, a histamine receptor, a leukotriene, a leukotriene receptor. The nucleic acid is present in an amount effective for preventing an allergic response in a mammal. Such amount can be readily determined based upon the teachings disclosed herein. Further, the composition comprises a pharmaceutically-acceptable carrier.

The invention further includes a pharmaceutical composition comprising at least one protein in an amount effective for treating an allergy in a mammal. The protein is selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor. The interleukin receptor is selected from the group consisting a receptor for an interleukin involved in the production of IgE in a mammal (e.g., IL-3, IL-4, IL-5, IL-6, IL-10, and IL-13). The composition further comprises a pharmaceutically acceptable carrier.

The invention further includes a pharmaceutical composition comprising at least one antibody that specifically binds to at least one interleukin involved in IgE production (i.e., IL-3, IL-4, IL-5, IL-6, IL-10, and IL-13) and a second protein in an amount effective for treating an allergy in a mammal selected from the group consisting of an anti-IgE antibody, an anti-IgE receptor antibody, a soluble IgE receptor, an anti-interleukin receptor antibody, a soluble interleukin receptor, an anti-interferon-alpha antibody, an anti-interferon-alpha receptor antibody, a soluble interferon-alpha receptor, an anti-histamine antibody, an anti-histamine receptor antibody, a soluble histamine receptor, an anti-leukotriene antibody, an anti-leukotriene receptor antibody, and a soluble leukotriene receptor. The interleukin receptor is selected from the group consisting a receptor for an interleukin involved in the production of IgE in a mammal (e.g., IL-3, IL-4, IL-5, IL-6, IL-10, and IL-13). The composition further comprises a pharmaceutically acceptable carrier.

The invention includes that the above-disclosed pharmaceutical compositions each can comprise interferon gamma.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Alleviate," as the term is used herein, means reducing the severity of the symptoms of the disease or disorder.

"Allergy vaccine," as the term is used herein, means an immunogenic substance which when administered to a human or veterinary patient, induces a detectable immune response to the substance thereby mediating a decrease in the amount of circulating IgE or in the level of IL-4 or IL-5 compared to the level of circulating IgE or in the level of IL-4 or IL-5 in the human or veterinary patient prior to the administration of the immunogenic substance or when compared to the level of circulating IgE or the level of IL-4 or IL-5 in an otherwise identical human or veterinary patient to which the immunogenic substance is not administered. Such immunogenic substance includes IgE, an IgE receptor, an interleukin involved in production of IgE in a mammal, a receptor for an interleukin involved in production of IgE in a mammal, histamine, a histamine receptor, a leukotriene, a leukotriene receptor, and any combination thereof.

An "amount effective for" treating an allergy and/or preventing an allergic response, as the term is used herein, means a quantity of a protein, peptide, and fragment thereof, or nucleic acid encoding the protein, peptide, and fragment thereof, and/or an antisense nucleic acid complementary to such nucleic acid, which when administered to a mammal, inhibits the production of IgE or reduces the level of IgE in a mammal. Further, as stated previously elsewhere herein, the amount of IgE produced and/or present in a mammal can be easily assessed using a wide variety of methods well-known in the art.

The term "antibody", as used herein, refers to an immunoglobulin molecule which is able to specifically bind to a specific epitope on an antigen.

Antibodies can be intact immunoglobulins derived from natural sources or from recombinant sources and can be immunoreactive portions of intact immunoglobulins.

Antibodies are typically tetramers of immunoglobulin molecules. The antibodies in the present invention may exist in a variety of forms including, for example, polyclonal antibodies and humanized antibodies (Harlow et al., 1999, In: Using Antibodies: A Laboratory Manual, Cold Spring Harbor, N.Y.; Harlow et al., 1988, In: Antibodies: A Laboratory Manual, Cold Spring Harbor, N.Y.; Houston et al., 1988, Proc. Natl. Acad. Sci. U.S.A. 85:5879–5883; Bird et al., 1988, Science 242:423–426).

By the term "specifically binds", as used herein, is meant, for example, an antibody which recognizes and binds an interleukin involved in IgE production, but does not substantially recognize or bind other molecules in a sample.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "antisense nucleic acid" means a nucleic acid polymer, at least a portion of which is complementary to another nucleic acid. The antisense nucleic acid may comprise between about fourteen and about fifty or more nucleotides. Preferably, the antisense nucleic acid comprises between about twelve and about thirty nucleotides. More preferably, the antisense nucleic acid comprises between about sixteen and about twenty-one nucleotides. The antisense nucleic acid may include, but is not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. : 5,034,506; Nielson et al., 1991, Science 254:1497).

The term "antisense" refers particularly to the nucleic acid sequence of the non-coding strand of a double stranded DNA molecule or, in the case of some viruses, a single or double stranded RNA molecule, encoding a protein, or to a sequence which is substantially homologous to the non-coding strand. It is not necessary that the antisense sequence be complementary solely to the coding portion of the coding strand of the nucleic acid molecule. The antisense sequence may be complementary to regulatory sequences specified on the coding strand of a nucleic acid molecule encoding a protein, which regulatory sequences control expression of the coding sequences.

The term "sense", as used herein, refers to the nucleic acid sequence of the single or double-stranded nucleic acid molecule which encodes a protein, or a sequence which is substantially homologous to that strand. However, the nucleic acid sequence is not limited solely to the portion of the coding strand encoding a protein; rather, the sequence may include regulatory sequences involves in, for example, the control of expression of the coding sequence.

By the term "applicator" as the term is used herein, is meant any device including, but not limited to, a hypodermic syringe, a pipette, a dropper, and the like, for administering the isolated nucleic acid, polypeptide or antibody to a cell or to an animal.

By the terms "coding" and "encoding," as these terms are used herein, is meant that the nucleotide sequence of a nucleic acid is capable of specifying a particular polypeptide of interest. That is, the nucleic acid may be transcribed and/or translated to produce the polypeptide. Thus, for example, an isolated nucleic acid encoding an interleukin is capable of being transcribed and/or translated to produce an interleukin polypeptide. Similarly, an isolated nucleic acid encoding an anti-interleukin compound is capable of being transcribed and/or translated to produce an anti-interleukin polypeptide, e.g., an interleukin receptor.

"Complementary" as used herein refers to the broad concept of subunit sequence complementary between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "immunogenic interleukin" as used herein, is meant an interleukin which when introduced into a human elicits at least one of a humoral or a cellular immune response which is specifically directed (i.e., would not be elicited but for the presence of the introduced interleukin) against the immunogenic interleukin.

Further, the term "immunogenic interleukin" should be construed to encompass not only polypeptide molecules, or fragments thereof, but should also be construed to encompass a nucleic acid encoding the interleukin or its receptor, whether as naked DNA or comprising a vector. The term should also be construed to encompass a cell expressing the interleukin of interest and/or an interleukin receptor such that the immunogenic interleukin is presented to the immune system so that a detectable immune response, whether humoral and/or cellular, to the interleukin and/or to an interleukin receptor is generated.

The term "interferon" or "IFN," as used interchangeably herein, refers to any know subtype of interferon. For example, "interferon-alpha" includes any of the fifteen known subtypes of interferon-alpha (IFNα), or any that may be determined in the future.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus; or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The use of the terms "nucleic acid encoding" or "nucleic acid coding" should be construed to include the RNA or DNA sequence which encodes the desired protein and any necessary 5' or 3' untranslated regions accompanying the actual coding sequence.

As used herein, the term "pharmaceutically-acceptable carrier" means a chemical composition with which an appropriate anti-interleukin compound may be combined and which, following the combination, can be used to administer the anti-interleukin compound to a patient.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "receptor" is a protein found on the surface of a cell or in its cytoplasm, that has a binding site with high affinity to a particular substance (e.g., a cytokine, a hormone, a neurotransmitter, and the like), referred to as the receptor's "ligand." By competitively inhibiting the ability of the receptor to bind its cognate ligand, such as by using, for example, an antibody to the ligand, an antibody to the receptor, or an analog of the receptor (e.g. a soluble receptor not associated with a cell or a cell surface), a receptor/ligand interaction required for induction of IgE production is inhibited thereby inhibiting or reducing the production of IgE.

By the term "scFv/phage" are used herein, is meant a phage particle which expresses the Fv portion of an antibody as a single chain.

As used herein, to "treat" means reducing the frequency with which symptoms of the allergy disease are experienced by a patient.

By the term "vaccine," as the term is used herein, is meant a protein, or fragment thereof, which when administered to a human or veterinary patient, induces a detectable immune response, humoral and/or cellular, to at least one protein or a fragment thereof.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the interleukin protein or nucleic acid encoding the interleukin, to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Sample protocols which employ the methods of the invention are now disclosed.

The patient is immunized with at least one appropriate interleukin, or combination thereof, either co-administered or wherein one interleukin is administered before the other. The interleukin (either as protein or nucleic acid encoding same) is administered parenterally (subcutaneously or intramuscularly) in doses of approximately 0.01 to about 1 mg/kg.

Immune plasma is collected from the patient immunized as disclosed above and administered parenterally to a patient suffering from an allergy. The immune plasma is used to confer passive immunity to the interleukin(s) of interest to patients suffering from an allergy. More specifically, the plasma is administered to a patient suffering from asthma.

Alternatively, anti-interleukin antibodies are purified from the immune plasma before being used to confer passive immunity to the interleukin.

Anti-interleukin antibody is administered intramuscularly (IM) or intravenously (IV) in doses of approximately 0.1 to about 100 mg/kg.

Anti-interleukin antibody is administered as disclosed above, and then, about 12 hours to about 96 hours after this, gamma interferon is administered IM in doses of about 1 to about $3 \times 10^6$ IU/kg body weight.

An interleukin receptor and/or an antibody to an interleukin receptor is administered IM or IV in doses of approximately 0.01 to about 1 mg/kg.

Interleukin receptor is administered, and then, about 12 hours to about 96 hours after this, INFγ interferon is administered IM in doses of about 1 to about $3 \times 10^6$ IU/kg body weight.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating an allergy in a mammal, said method comprising administering to said mammal an anti-histamine antibody and interferon gamma, thereby treating an allergy in a mammal.

2. A kit for treating an allergy in a mammal, said kit comprising an anti-histamine antibody, interferon gamma, an applicator, and an instructional material for the use thereof.

3. A pharmaceutical composition comprising a protein in an amount effective for treating an allergy in a mammal, wherein said protein is an anti-histamine antibody in a pharmaceutically acceptable carrier, said pharmaceutical composition further comprising interferon gamma.

* * * * *